(12) United States Patent
Zastrozna et al.

(10) Patent No.: US 11,806,050 B2
(45) Date of Patent: Nov. 7, 2023

(54) TENSION ISOLATING ADJUSTABLE ADAPTER FOR EXTERNAL FIXATION AND METHODS OF PRODUCTION AND USE THEREOF

(71) Applicant: DePuy Synthes Products, Inc., Raynham, MA (US)

(72) Inventors: Anna Zastrozna, West Chester, PA (US); James Amis, West Chester, PA (US); Michael Wahl, West Chester, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 546 days.

(21) Appl. No.: 17/027,018

(22) Filed: Sep. 21, 2020

(65) Prior Publication Data
US 2022/0087719 A1    Mar. 24, 2022

(51) Int. Cl.
A61B 17/64    (2006.01)
A61B 17/66    (2006.01)
A61B 5/053    (2021.01)
A61B 5/00    (2006.01)
A61B 17/88    (2006.01)

(52) U.S. Cl.
CPC .............. *A61B 17/66* (2013.01); *A61B 5/053* (2013.01); *A61B 5/4851* (2013.01); *A61B 17/64* (2013.01); *A61B 17/8869* (2013.01)

(58) Field of Classification Search
None
See application file for complete search history.

(56) References Cited

U.S. PATENT DOCUMENTS

| | | | |
|---|---|---|---|
| 4,699,616 A | * | 10/1987 | Nowak ................. A61M 25/02 128/DIG. 26 |
| 5,281,221 A | | 1/1994 | Tadych |
| 5,360,020 A | | 11/1994 | Lee, Sr. et al. |

(Continued)

FOREIGN PATENT DOCUMENTS

| | | |
|---|---|---|
| CN | 2282410 | 5/1998 |
| CN | 103393492 | 11/2013 |

(Continued)

OTHER PUBLICATIONS

Van der Borden et al., Prevention of pin tract infection in external stainless steel fixator frames using electric current in a goat model, sciencedirect.com, Jan. 4, 2007.*

(Continued)

*Primary Examiner* — Jan Christopher L Merene
(74) *Attorney, Agent, or Firm* — Dunlap Codding, P.C.

(57) ABSTRACT

Tension isolating adjustable adapters are disclosed, along with kits and systems containing same, as well as methods of production and use thereof. The tension isolating adjustable adapters include a percutaneous device holder that can be releasably connected to a percutaneous device via a locking element, and a tensioning member that engages the percutaneous device holder. The tensioning member has at least one tension pad that is shaped and configured to be disposed about the percutaneous device insertion site in the patient's skin, and the engagement of the tensioning member(s) to the percutaneous device holder allows for adjustment of the tension pad(s).

21 Claims, 13 Drawing Sheets

(56) References Cited

U.S. PATENT DOCUMENTS

| | | | |
|---|---|---|---|
| 5,447,492 A * | 9/1995 | Cartmell | A61F 13/0203 602/41 |
| 5,702,388 A | 12/1997 | Jackson et al. | |
| 5,906,600 A | 5/1999 | Bähr | |
| 7,834,232 B2 | 11/2010 | Rastegar et al. | |
| 8,135,466 B2 | 3/2012 | Fuller et al. | |
| 8,389,791 B2 | 3/2013 | Gurtner et al. | |
| 8,840,611 B2 | 9/2014 | Mullaney et al. | |
| 9,616,142 B2 | 4/2017 | Ehrensberger et al. | |
| 9,913,758 B2 | 3/2018 | Rastegar et al. | |
| 10,004,916 B2 | 6/2018 | Rogachefsky et al. | |
| 10,226,214 B2 | 3/2019 | Ogrodnik et al. | |
| 2003/0036761 A1 | 2/2003 | Smothers et al. | |
| 2009/0318842 A1 | 12/2009 | Kairinos | |
| 2010/0204802 A1 | 8/2010 | Wilson et al. | |
| 2016/0213522 A1 * | 7/2016 | Gurtner | C07K 5/06113 |
| 2016/0303350 A1 * | 10/2016 | Konstantarakis | A61M 39/0247 |
| 2017/0056536 A1 | 3/2017 | Hallab et al. | |
| 2018/0185196 A1 | 7/2018 | Levinson et al. | |
| 2019/0015255 A1 | 1/2019 | Gurtner et al. | |
| 2020/0155198 A1 | 5/2020 | Sanders, Jr. | |
| 2021/0059554 A1 * | 3/2021 | Armbruster | A61B 17/64 |
| 2021/0100587 A1 * | 4/2021 | Zastrozna | A61B 17/66 |

FOREIGN PATENT DOCUMENTS

| | | |
|---|---|---|
| DE | 3729253 A1 | 3/1989 |
| EP | 2384168 A1 | 11/2011 |
| IN | 2008CH00979 | 10/2009 |
| WO | 199844967 | 10/1998 |
| WO | 2013038182 A3 | 3/2013 |
| WO | 2016113440 A1 | 7/2016 |

OTHER PUBLICATIONS

Van Der Borden, et al.; "Detection, Prevention, and Direct Post-Operative Intervention in Orthopedic Implant Infection," University of Groningen (2007), pp. 125-138.

International Search Report, dated Nov. 17, 2021, in PCT/IB2021/057909, filed Aug. 30, 2021.

Written Opinion of the International Searching Authority, dated Nov. 17, 2021, in PCT/IB2021/057909, filed Aug. 30, 2021.

* cited by examiner

TENSION ISOLATING ADJUSTABLE ADAPTER FOR EXTERNAL FIXATION AND METHODS OF PRODUCTION AND USE THEREOF

CROSS REFERENCE TO RELATED APPLICATIONS/INCORPORATION BY REFERENCE STATEMENT

Not Applicable.

STATEMENT REGARDING FEDERALLY SPONSORED RESEARCH OR DEVELOPMENT

Not Applicable.

BACKGROUND

Percutaneous devices, such as (but not limited to) pins, screws, and wires, are commonly used in orthopedic procedures to stabilize and/or correct fractures, injuries, and defects. Particular examples of percutaneous devices include (but are not limited to) skeletal traction pins, percutaneous fracture pinning, and external fixation devices. However, these devices can cause excessive skin tension at their insertion sites, and this tension can decrease blood supply and lead to necrosis of the surrounding tissue, thus acting as a 'magnet' for infection at the insertion site.

For example, external fixation of bone fractures commonly involves the long-term use of orthopedic pins inserted into the bone fragments and fixed to the external structure. The pins stress the skin around them during bone distraction, external fixation adjustment, or patient movement, often leading to the cutting or tearing of pin tracks in the skin, along with the subsequent infection associated therewith. Indeed, one study reported site infection as the most common complication of external fixation, with an 11.3% to 100% infection rate in the study group (Kazmers et al., (2016) *Strat Traum Limb Recon,* 11:75-85).

Currently, clinicians recommend a variety of techniques to try to prevent pin track infection, including local antiseptics and regular pin site cleaning. Despite aggressive treatments, however, pin track infection is still the most common complication of external fixation. In addition, the risk of pin track infection increases with time; the longer an external fixation pin remains in place, the higher the risk of infection and the more severe the infections become. With more recently developed surgical treatments such as distraction osteogenesis, external fixation pins can remain in place for many months. The success of these distraction osteogenesis procedures depends upon the ability to maintain the fixation pins infection-free for long periods. Pin track infection can decrease the stability of the fixator pin-bone interface, which creates an unsuitable environment for optimal bone healing and can lead to pin loosening, fracture non-union, and chronic osteomyelitis (Ferreira and Marais (2012) Strategies Trauma Limb Reconstr, 7(2): 67-72). While soft tissue infection can often be treated effectively with oral antibiotics and local skin treatment, deeper bone infection might require removal of percutaneous pins or abandonment of external fixation altogether, potentially causing delays in the overall bone healing process.

Therefore, there is a need in the art for new and improved devices and methods of using same around the insertion sites of percutaneous devices, to reduce skin tension and the cutting/tearing of skin in response to bone distraction, external fixation adjustment, gravity, or patient movement, and thus reduce the risk of infection related thereto. It is to such devices, as well as methods of producing and using same, that the present disclosure is directed.

DETAILED DESCRIPTION

Figure 1:
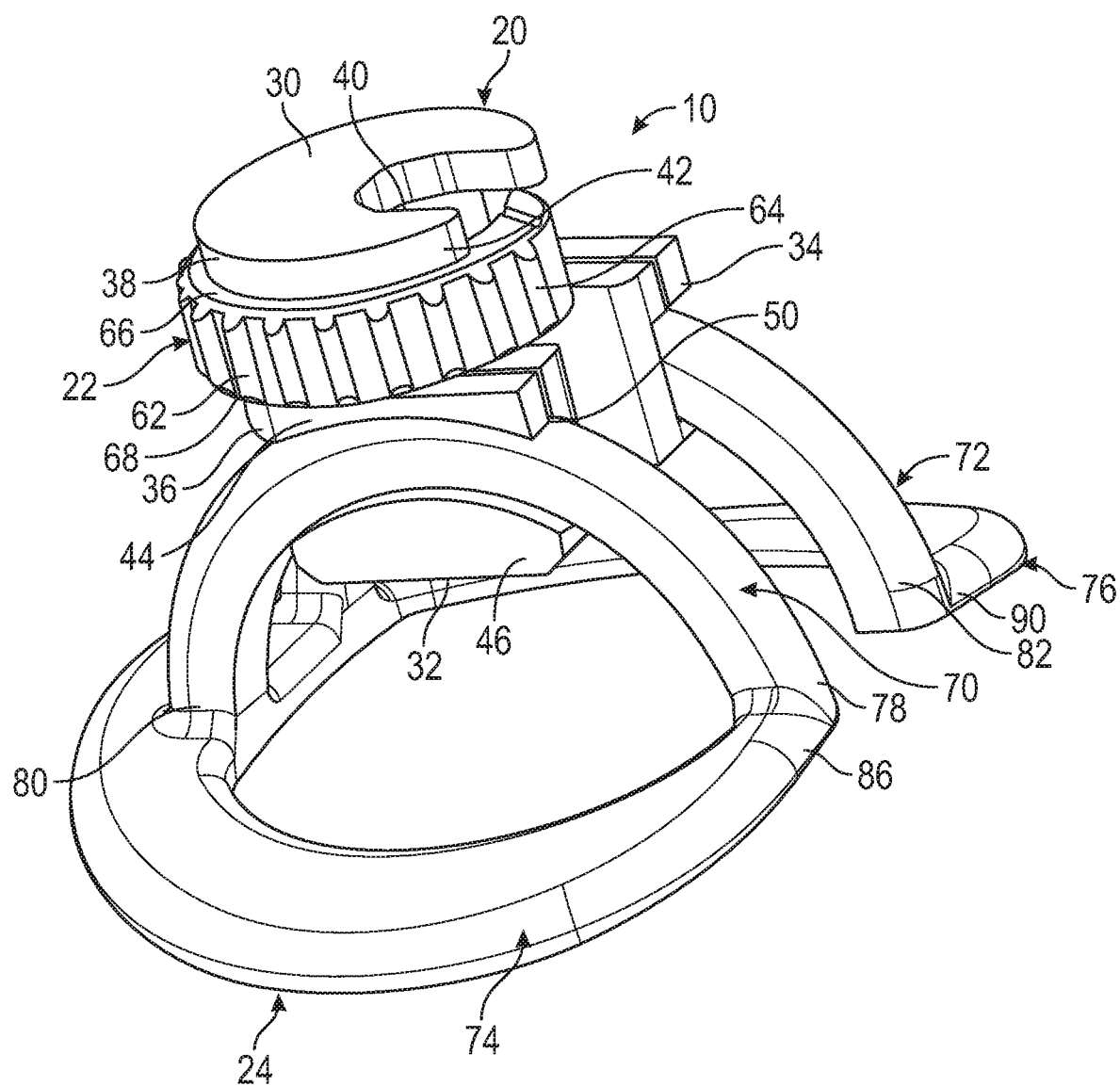
FIG. 1 is a perspective view of one non-limiting embodiment of a tension isolating adjustable adapter constructed in accordance with the present disclosure.

Before explaining at least one embodiment of the present disclosure in detail by way of exemplary language and results, it is to be understood that the present disclosure is not limited in its application to the details of construction and the arrangement of the components set forth in the following description. The present disclosure is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the present disclosure shall have the meanings that are commonly understood by those of ordinary skill in the art. Further, unless otherwise required by context, singular terms shall include pluralities and plural terms shall include the singular. The foregoing techniques and procedures are generally performed according to conventional methods well known in the art and as described in various general and more specific references that are cited and discussed throughout the present specification. The nomenclatures utilized in connection with, and the medical procedures and techniques of, surgery, anesthesia, wound healing, and infectious control described herein are those well-known and commonly used in the art. Standard techniques are used for infection diagnostic and therapeutic applications.

All patents, published patent applications, and non-patent publications mentioned in the specification are indicative of the level of skill of those skilled in the art to which the present disclosure pertains. All patents, published patent applications, and non-patent publications referenced in any portion of this application are herein expressly incorporated by reference in their entirety to the same extent as if each individual patent or publication was specifically and individually indicated to be incorporated by reference.

All of the articles, compositions, kits, and/or methods disclosed herein can be made and executed without undue experimentation in light of the present disclosure. While the articles, compositions, kits, and/or methods have been described in terms of particular embodiments, it will be apparent to those of skill in the art that variations may be applied to the articles, compositions, kits, and/or methods and in the steps or in the sequence of steps of the methods described herein without departing from the concept, spirit, and scope of the present disclosure. All such similar substitutions and modifications apparent to those skilled in the art are deemed to be within the spirit, scope, and concept of the present disclosure as defined by the appended claims.

As utilized in accordance with the present disclosure, the following terms, unless otherwise indicated, shall be understood to have the following meanings:

The use of the term "a" or "an" when used in conjunction with the term "comprising" in the claims and/or the specification may mean "one," but it is also consistent with the meaning of "one or more," "at least one," and "one or more than one." As such, the terms "a," "an," and "the" include plural referents unless the context clearly indicates otherwise. Thus, for example, reference to "a compound" may refer to one or more compounds, two or more compounds, three or more compounds, four or more compounds, or greater numbers of compounds. The term "plurality" refers to "two or more."

The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y, and Z" will be understood to include X alone, Y alone, and Z alone, as well as any combination of X, Y, and Z.

The use of ordinal number terminology (i.e., "first," "second," "third," "fourth," etc.) is solely for the purpose of differentiating between two or more items and, unless explicitly stated otherwise, is not meant to imply any sequence or order or importance to one item over another or any order of addition, for example.

The use of the term "or" in the claims is used to mean an inclusive "and/or" unless explicitly indicated to refer to alternatives only or unless the alternatives are mutually exclusive. For example, a condition "A or B" is satisfied by any of the following: A is true (or present) and B is false (or not present), A is false (or not present) and B is true (or present), and both A and B are true (or present).

As used herein, any reference to "one embodiment," "an embodiment," "some embodiments," "one example," "for example," or "an example" means that a particular element, feature, structure, or characteristic described in connection with the embodiment is included in at least one embodiment. The appearance of the phrase "in some embodiments" or "one example" in various places in the specification is not necessarily all referring to the same embodiment, for example. Further, all references to one or more embodiments or examples are to be construed as non-limiting to the claims.

Throughout this application, the term "about" is used to indicate that a value includes the inherent variation of error for a composition/apparatus/device, the method being employed to determine the value, or the variation that exists among the study subjects. For example, but not by way of limitation, when the term "about" is utilized, the designated value may vary by plus or minus twenty percent, or fifteen percent, or twelve percent, or eleven percent, or ten percent, or nine percent, or eight percent, or seven percent, or six percent, or five percent, or four percent, or three percent, or two percent, or one percent from the specified value, as such variations are appropriate to perform the disclosed methods and as understood by persons having ordinary skill in the art.

As used in this specification and claim(s), the words "comprising" (and any form of comprising, such as "comprise" and "comprises"), "having" (and any form of having, such as "have" and "has"), "including" (and any form of including, such as "includes" and "include"), or "containing" (and any form of containing, such as "contains" and "contain") are inclusive or open-ended and do not exclude additional, unrecited elements or method steps. For example, a process, method, article, or apparatus that comprises a list of elements is not necessarily limited to only those elements but may include other elements not expressly listed or inherently present therein.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used herein, the term "substantially" means that the subsequently described event or circumstance completely occurs or that the subsequently described event or circumstance occurs to a great extent or degree. For example (but not by way of limitation), when associated with a particular event or circumstance, the term "substantially" means that the subsequently described event or circumstance occurs at least 80% of the time, or at least 85% of the time, or at least 90% of the time, or at least 95% of the time. The term "substantially adjacent" may mean that two items are 100% adjacent to one another, or that the two items are within close proximity to one another but not 100% adjacent to one another, or that a portion of one of the two items is not 100% adjacent to the other item but is within close proximity to the other item.

As used herein, the phrases "associated with," "coupled to," and "connected to" include both direct association/coupling/connection of two elements to one another as well as indirect association/coupling/connection of two elements to one another. When two elements are indirectly associated/coupled/connected to one another, one or more intervening elements may be present therebetween. Non-limiting examples of intervening elements include washers, sleeves, fasteners, nuts, bolts, anchors, nails, inserts, rivets, bonding materials, and the like.

As used herein, the term "patient" or "subject" is meant to include all organisms, whether alive or dead, including any species having soft tissues and bones. For example, a system according to the inventive concepts disclosed herein may be applied to the skin of a living human, horse, cow, sheep, cat, dog, and the like.

The term "percutaneous device" as used herein refers to devices commonly used in orthopedic procedures to stabilize and/or correct fractures, injuries, and defects. The term "percutaneous device" includes any device that is capable of being fixated within a patient (i.e., capable of being inserted through the skin and tissue of a patient and into a bone thereof). Particular examples of types of percutaneous devices include (but are not limited to) skeletal traction pins, percutaneous fracture pinning, and external fixation devices. Particular non-limiting examples of percutaneous devices that may be utilized in accordance with the present disclosure include pins, screws, and wires. These percutaneous devices may be formed of metallic, polymeric, and/or biodegradable materials.

The term "external fixation member" as used herein refers to a type of percutaneous device attached to a rigid external frame. The rigid external frame provides further stability to the percutaneous devices and also allows the devices to be adjusted externally, if desired, to ensure the bones remain in an optimal position during the healing process. In a particular (but non-limiting) embodiment, the term "external fixation member" also includes percutaneous devices to which a distraction force may be applied.

The term "distraction" as used herein may in some non-limiting embodiments refer to the process of distraction osteogenesis, in which a distraction force is applied to two (or more) external fixation members in opposite directions so as to slowly pull the two bone segments apart. As the bone segments are pulled apart, osteogenesis occurs, and new bone is formed in the gap produced by the distraction forces, thus rejoining the bone segments. In distraction osteogenesis, the distraction forces are typically applied slowly over time, so as to allow the new bone to grow and harden over time. Typically, this process takes a period of time in a range of from about one month to about six months, or even longer, depending on the process. However, as the distraction forces pull the two bone segments apart, the external fixation members move through the skin and cut the skin in the process. That is, an area of the skin around the leading edge of each external fixation member is stretched until the skin cuts or tears and forms a pin track.

Pin tracks, whether formed simply from patient movement or gravity or in response to an external source (such as, but not limited to, external fixation adjustment or distraction), are highly prone to infection. Infections at these percutaneous device insertion sites can potentially have a devastating effect on the success of the healing process.

Therefore, the present disclosure is directed to an apparatus/assembly and methods that reduce the risk of pin track infection. This is accomplished by morphing and/or distributing the tension formed in the skin around the percutaneous insertion sites and thereby reducing the incidence (and/or length) of pin tracks being formed in the skin.

In particular (but not by way of limitation), the present disclosure includes a tension isolating adjustable adapter that can be utilized for external fixation. The tension isolating adjustable adapter has a portion thereof (i.e., one or more tension pads) that contacts the skin of a patient around the insertion site of a percutaneous device with a sufficient amount of pressure so as to maintain the skin disposed between the percutaneous device and the tension pad(s) in a substantially taut orientation and thereby distribute any force exerted by the percutaneous device around the area of skin disposed between the percutaneous device insertion site and the tension pad(s). In this manner, the adapter transmits the force(s) from the percutaneous device to the area of skin, thus bypassing the incision/insertion sites (note that the force(s) from the percutaneous device may simply be due to gravity or patient movement, or may be the result of manipulation(s) such as (but not limited to) external fixation movement/adjustment or distraction). This is an important feature associated with the use of these tension isolating adjustable adapters, because minimizing stress at the pin incision sites reduces the amount of force felt by the skin insertion sites and further protects the skin insertion sites from cutting/tearing, thereby further reducing morbidity and risk of infections. In addition, the tension isolating adjustable adapter of the present disclosure allows for adjustment to skin shape, thereby allowing the portion of the adapter that contacts the skin to be able to contact the skin along substantially all of the skin area under the adapter. Also, the tension isolating adjustable adapter can be adjusted to various angles of pin insertion. Further, the adapter can provide easy access and/or be removed for wound care at the incision/insertion site while the percutaneous device remains in place. This is an important feature of the presently disclosed adapters, as percutaneous devices may be retained in position fixated within the body of the patient fora significant period of time (such as, but not limited to, a period within a range of from about 14 days to about 6 months, or even longer). The ability to provide wound care at the incision/insertion site will greatly increase the chance of success of healing.

Certain non-limiting embodiments of the present disclosure are directed to a tension isolating adjustable adapter for use with a percutaneous device. The adapter includes a percutaneous device holder, a tensioning member, and a locking element. The percutaneous device holder has a recess sized and shaped to receive a portion of a percutaneous device. In addition, the percutaneous device holder includes at least a first groove and a second groove (which may each be independently formed on an outer and/or inner surface thereof). The tensioning member is releasably connected or coupled to the percutaneous device holder. The tensioning member has at least one guide rail and at least one tension pad coupled to the guide rail. The at least one guide rail is releasably inserted into the second groove of the percutaneous device holder. The at least one tension pad is shaped and configured to be disposed about an insertion site of the percutaneous device into a patient's skin. The at least one guide rail engages the second groove of the percutaneous device holder in a manner that allows for adjustment of the at least one tension pad (for example (but not by way of limitation), adjustment with respect to the percutaneous device, the percutaneous device holder, and/or the patient's skin). The locking element is connected or coupled to the first groove of the percutaneous device holder and is shaped and configured to secure the percutaneous device holder to the percutaneous device. In particular, the locking element provides a mechanism for adjusting and securing the portion of the percutaneous device in place within the percutaneous device holder.

In addition, the at least one tension pad is designed to contact the patient's skin with a sufficient amount of pressure so as to maintain the skin disposed between the at least one tension pad and the percutaneous device insertion site in a substantially taut orientation and thereby distribute any force exerted by the percutaneous device around the area of skin disposed between the percutaneous device insertion site and the at least one tension pad.

It should be understood that each component of the tension isolating adjustable adapter may be formed of one or more materials and may have one or more parts/elements. In addition, each component of the tension isolating adjustable adapter may be substantially rigid, partially flexible, or substantially flexible.

In certain particular (but non-limiting) embodiments, the tensioning member is further defined as having a first guide rail, a second guide rail, a first tension pad, and a second tension pad, wherein the first tension pad is coupled to the first guide rail, and the second tension pad is coupled to the second guide rail. The first and second guide rails are spaced apart from one another in a parallel relationship, and the first and second guide rails can be releasably inserted into opposite sides of the second groove of the percutaneous device holder. The first and second tension pads are each shaped and configured to be disposed about the percutaneous device's insertion site into the patient's skin, wherein each of the first and second guide rails engages the second groove of the percutaneous device holder and allows for adjustment of the first or second tension pad (for example (but not by way of limitation), adjustment with respect to the percutaneous device, the percutaneous device holder, and/or the patient's skin). In addition, the first and second tension pads are designed to contact the patient's skin with a sufficient amount of pressure so as to maintain the skin disposed between the first and second tension pads in a substantially taut orientation and thereby distribute any force exerted by the percutaneous device around the area of skin disposed between the first and second tension pads.

The tension isolating adjustable adapter allows for adjustment of the adapter with respect to both the percutaneous device and the patient's skin. For example (but not by way of limitation), the tension pad(s) is adjustable to a shape of the patient's skin surface. In addition, in certain non-limiting embodiments, the tension pad(s) is substantially anatomically-shaped. Also, the tension pad(s) can be adjustable to an insertion angle of the percutaneous device.

In certain non-limiting embodiments, the locking element of the tension isolating adjustable adapter secures the percutaneous device holder in position, and the tensioning member is secured in place upon the patient's skin simply via pressure/friction upon the locking element securing the percutaneous device holder in position. Alternatively (and or in addition thereto), the locking element of the tension isolating adjustable adapter can secure both the percutaneous device holder and the tensioning member in position upon independent positioning and placement of each of these elements. For example (but not by way of limitation), the percutaneous device holder may be secured in place about the percutaneous device as discussed in detail herein above, and the locking element can also engage the at least one guide rail of the tensioning member and secure the tensioning member in position with respect to the percutaneous device holder (as well the patient's skin).

In certain non-limiting embodiments, the tension isolating adjustable adapter is releasably secured to the percutaneous device. The ability to remove the adapter allows for effective wound care at the incision site while the percutaneous/external fixation device remains in place.

Each of the locking element and the guide rail(s) of the tensioning member engage the first and second grooves, respectively, of the percutaneous device holder by any mechanisms known in the art or otherwise contemplated herein. For example (but not by way of limitation), the locking element and/or guide rail may slidably engage the corresponding groove of the percutaneous device holder, or the engagement may involve a ratchet mechanism.

Certain embodiments of the present disclosure are further directed to a kit that includes one or more of any of the tension isolating adjustable adapters discussed in detail herein above or otherwise contemplated herein. The kit may also include at least one percutaneous device for use with any of the tension isolating adjustable adapters present in the kit.

In a particular (but non-limiting) embodiment, the kit may further include one or more segments of the elastically deformable membrane, as described in detail in U.S. Ser. No. 16/590,810, filed Oct. 2, 2019. Alternatively (and/or in addition thereto), the kit may further include at least one electrical device for monitoring, preventing, and/or treating implant infections, as described in detail in U.S. Ser. No. 16/999,597, filed Aug. 21, 2020. The entirety of each of the above-referenced applications are hereby expressly incorporated herein by reference. In particular, the elastically deformable membrane(s) typically has a bonding material attached to at least a portion of a surface thereof for connecting the membrane to a patient's skin. Also, the electrical device typically includes a housing; a power source configured to supply electrical power to a conductive percutaneous implant in a circuit including the conductive percutaneous implant and tissue of a patient adjacent to the conductive percutaneous implant; an electrical sensor configured to generate a signal indicative of at least one electrical parameter of the circuit; and at least one data processing system having one or more processors configured to receive the signal and analyze the signal to determine at least one of a presence or change of infection of the tissue, and pass a control signal to the power source to vary the electrical power responsive to determining at least one of the presence or change of infection of the tissue.

In addition, the kit may further contain one or more other component(s) or reagent(s) that may be utilized with the tension isolating adjustable adapters in accordance with the present disclosure. The nature of these additional component (s)/reagent(s) will depend upon various factors, and identification thereof is well within the skill of one of ordinary skill in the art; therefore, no further description thereof is deemed necessary.

Also, the various components/reagents present in the kit may each be in separate containers/compartments, or various components/reagents can be combined in one or more containers/compartments. That is, the tension isolating adjustable adapter may be provided partially or fully assembled, or the tension isolating adjustable adapter may be provided in a disassembled form such that the percutaneous device holder, a locking element, and the tensioning member are packaged separately within the kit. In addition, the kit may include a set of written instructions explaining how to use the kit. A kit of this nature can be used in any of the methods described or otherwise contemplated herein.

Certain embodiments of the present disclosure are further directed to a system that includes any of the tension isolating adjustable adapters and any of the percutaneous devices discussed in detail herein above or otherwise contemplated herein. In certain non-limiting embodiments, the system may further include at least one segment of elastically deformable membrane and/or at least one electrical device for monitoring, preventing, and/or treating implant infections (as described in detail in U.S. Ser. No. 16/590,810 or U.S. Ser. No. 16/999,597, respectively, incorporated supra).

Any of the components of the tension isolating adjustable adapter or the kits/systems described herein may have an antimicrobial agent associated therewith. For example (but not by way of limitation), the tension pad(s) and/or the segment(s) of elastically deformable membrane may have an antimicrobial agent associated with at least a portion of a surface thereof.

Any antimicrobial agents known in the art or otherwise contemplatable by a person of ordinary skill in the art may be utilized in accordance with the present disclosure. For example (but not by way of limitation), the antimicrobial agent may be an antibacterial agent and/or an antifungal agent. Examples of antimicrobial and antibacterial agents are well known in the art, and a wide variety thereof are commercially available. Therefore, it is well within the common abilities of a person having ordinary skill in the art to identify and select particular antimicrobial and antibacterial agents that can be used in accordance with the present disclosure, given the particular uses for which the adapters are employed. As such, no further discussion thereon is deemed necessary.

Certain non-limiting embodiments of the present disclosure are directed to a method that comprises the steps of: (A) connecting a tension isolating adjustable adapter to a portion of a percutaneous device, inserting a portion of the percutaneous device through a skin of a patient, and fixating the inserted portion of the percutaneous device within a body of the patient, whereby the portion of the percutaneous device to which the tension isolating adjustable adapter is connected extends above the patient's skin; (B) adjusting the tension isolating adjustable adapter along the length of the percutaneous device until at least one tension pad of the tension isolating adjustable adapter contacts the skin of the patient; and (C) adjusting the at least one tension pad until the at least one tension pad contacts the patient's skin with a sufficient amount of pressure so as to maintain the skin disposed between an insertion site of the percutaneous device and the at least one tension pad in a substantially taut orientation and thereby distribute any force exerted by the percutaneous device around the area of skin disposed between the percutaneous device insertion site and the at least one tension pad.

In certain particular (but non-limiting) embodiments, the tension isolating adjustable adapter utilized in the method above may be any of the tension isolating adjustable adapters disclosed or otherwise contemplated herein.

The tension isolating adjustable adapter may be connected to the percutaneous device prior to inserting the percutaneous device through the patient's skin and fixating same within the patient's body. Alternatively, the tension isolating adjustable adapter may be connected to the percutaneous device after the percutaneous device is inserted through the patient's skin and fixated within the patient's body.

Any of the methods disclosed or otherwise contemplated herein may further comprise the step of: (D) adjusting a locking element of the tension isolating adjustable adapter to secure the tension isolating adjustable adapter in position about the percutaneous device, thereby maintaining the sufficient amount of pressure exerted by the at least one tension pad upon the patient's skin to provide the substantially taut orientation thereto.

Any of the methods disclosed or otherwise contemplated herein may further comprise the step of: (E) performing at least one external adjustment and/or applying at least one distraction force to the percutaneous device.

It will be understood that steps (D) and (E) above may not be present, or only one of these steps may be present, or both of these steps may be present. Therefore, the designation of these steps in alphabetical order is non-limiting; the scope of the present disclosure includes a method that does not include either of steps (D) and (E), a method that only includes step (D) without step (E), a method that only includes step (E) without step (D), and a method that includes both steps (D) and (E).

Any of the methods disclosed or otherwise contemplated herein may further include the use of one or more elastically deformable membranes, as described in detail in one or more segments of the elastically deformable membrane, as described in detail in U.S. Ser. No. 16/590,810, incorporated supra. For example (but not by way of limitation), the method further comprise the steps of: applying force to a segment of elastically deformable membrane to stretch the membrane to a stretched length that is greater than an original length of the membrane, wherein the elastically deformable membrane has a bonding material associated with at least a portion of a surface thereof; applying the stretched membrane to the patient's, wherein the bonding material attaches the stretched membrane to the skin; and releasing the stretch force on the membrane after application to the skin, thereby causing the skin having the membrane attached thereto to gather/compress. When these steps are present, they may be performed prior to, during, or after placement of the tension isolating adjuster adapter and the percutaneous device.

In certain non-limiting embodiments, the percutaneous device utilized is conductive, and the method may further include the steps of forming an electrical circuit to monitor, treat, and/or reduce the occurrence of implant infections, as described in detail in U.S. Ser. No. 16/999,597, incorporated supra. For example (but not by way of limitation), the method may further include the steps of: forming an electrical circuit at an insertion site of the percutaneous device through the patient's skin and fixated within the body, the electrical circuit including a power source, the conductive percutaneous device, and tissue surrounding the conductive percutaneous implant; monitoring at least one electrical parameter in the electrical circuit; determining a presence of an infection due to the electrical parameter; and varying electrical power within the electrical circuit responsive to determining the presence of the infection.

When the methods involve the use of one or more elastically deformable membranes and/or the use of the electrical device as described in the paragraph above, the method can further include the presence of step(s) (D) and/or (E), or be performed in the absence of steps (D) and (E). Also, the elastically deformable membranes and the electrical device may be used separately or together. As such, the scope of the present disclosure includes a method that includes only steps (A)-(C) above, as well as methods that include any combination of one or more (or even all) of the various other method steps (or combination(s) of method steps) described or otherwise contemplated herein.

For each of the methods described herein, two or more steps may be performed simultaneously or wholly or partially sequentially. In addition, one or more of the steps may be performed immediately following a prior step, and/or a period of time may pass in between two or more steps. For example (but not by way of limitation), the elastically deformable membrane may be applied to the skin and allowed to gather/stretch/compress the skin for a period of time (such as, but not limited to, about 1, 2, 3, 4, 5, 6, or 7 days or about 1, 2, 3, or 4 weeks, or any range thereof) prior to the surgical placement of the percutaneous device(s) and attachment of the tension isolating adjustable adapter thereto. Alternatively, the elastically deformable membrane could be applied to the skin during the surgical procedure and thus immediately prior to placement of the percutaneous device(s) and attachment of the tension isolating adjustable adapter.

Further, changes can be made in the order or sequence of steps, and one or more steps may be repeated, as desired, for any of the methods disclosed or otherwise contemplated herein.

Turning now to the Drawings, FIG. 1 illustrates one non-limiting embodiment of a tension isolating adjustable adapter 10 constructed in accordance with the present disclosure. The tension isolating adjustable adapter 10 is for use with a percutaneous device 12. The adapter includes a percutaneous device holder 20, a locking element 22, and a tensioning member 24.

Figure 2:
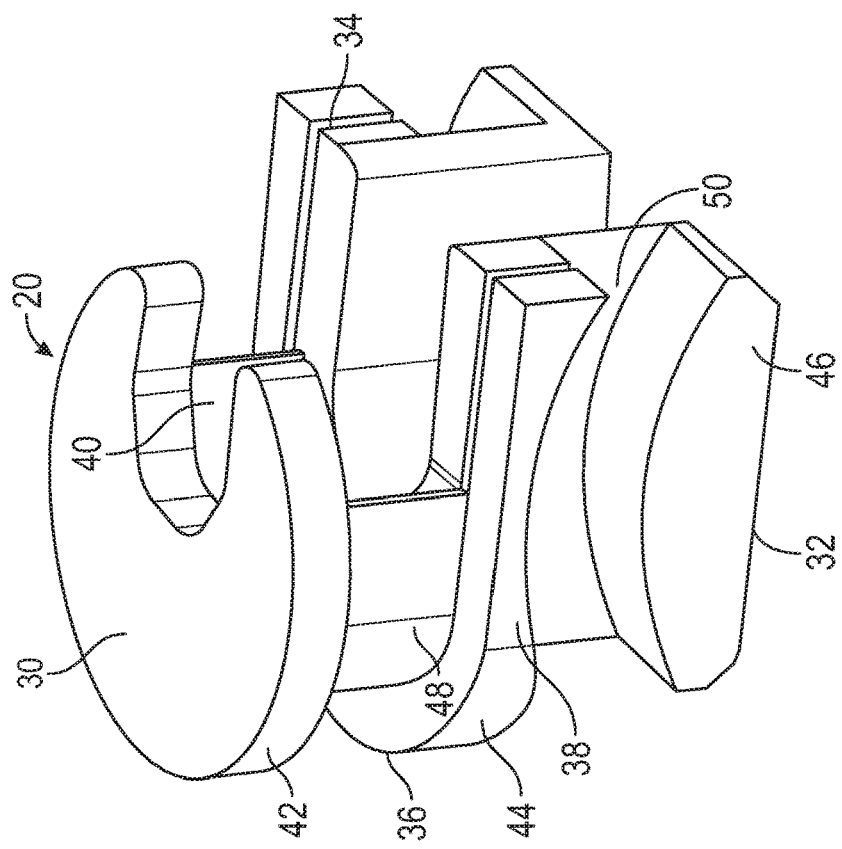
FIG. 2 is a perspective view of a percutaneous device holder of the tension isolating adjustable adapter of FIG. 1.

The percutaneous device holder 20 contacts the percutaneous device 12 and provides support for the tensioning member 22. As shown in FIGS. 1-2, the percutaneous device holder 20 has an upper end 30, a lower end 32, a front side 34, a back side 36, and an outer surface 38. At least a portion of the percutaneous device holder 20 generally has a semi-circular shape, C-shape, U-shape, or any other type of convex shape (or combinations thereof) in which a recess 40 is formed that extends from the upper end 30 to the lower end 32 thereof; the recess 40 is sized and shaped to receive a portion of the percutaneous device 12. In addition, the percutaneous device holder 20 includes a first flange 42, a second flange 44, and a third flange 46 that each extend from the outer surface 38 of the percutaneous device holder 20. An area in between the first and second flanges 42 and 44 forms a first groove 48 on the outer surface 38 of the percutaneous device holder 20, while an area between the second and third flanges 44 and 46 forms a second groove 50 on the outer surface 38 of the percutaneous device holder 20.

While the first flange 42 is illustrated in FIG. 2 as having a substantially semi-circular or C-shape, and the second and third flanges 44 and 46 are illustrated in FIG. 2 as each having a substantially horseshoe or U-shape, these configurations will be understood as being for purposes of illustration only. The various parts of the percutaneous device holder 20 may be provided with any size/shape, as well as any combination of sizes/shapes, that may be desired by a person of ordinary skill in the art. Indeed, the percutaneous device holder 20 may be provided with any size/shape (or combinations of sizes/shapes) that allow the percutaneous device holder 20 to interact with the percutaneous device 12, the locking element 22, and the tensioning member 24 in the manner and function as described or otherwise contemplated herein. In addition, while the flanges 42, 44, and 46 and the grooves 48 and 50 are depicted as continuously extending horizontally around the outer surface 38 of the percutaneous device holder 20, it will be understood that one or more of any of the flanges 42, 44, and 46 and the grooves 48 and 50 may only extend horizontally around a portion of the outer surface 38 of the percutaneous device holder 20. For example (but not by way of limitation), the second groove 50 may not extend fully to the back end 36 of the percutaneous device holder 20, but rather may comprise two separate grooves on either side of the percutaneous device holder 20 that do not connect in the back.

The locking element 22 is releasably connected or coupled to the percutaneous device holder 20 for adjusting and securing a portion of the percutaneous device 12 in place within the recess 40 of the percutaneous device holder 20. The locking element 22 slidably engages the first groove 48 of the percutaneous device holder 20, and the position/placement of the locking element 22 is adjusted until a portion of the recess 40 is covered by the locking element 22 so that a percutaneous device 12 disposed within the recess 40 is secured in place in the percutaneous device holder 20.

Figure 3:
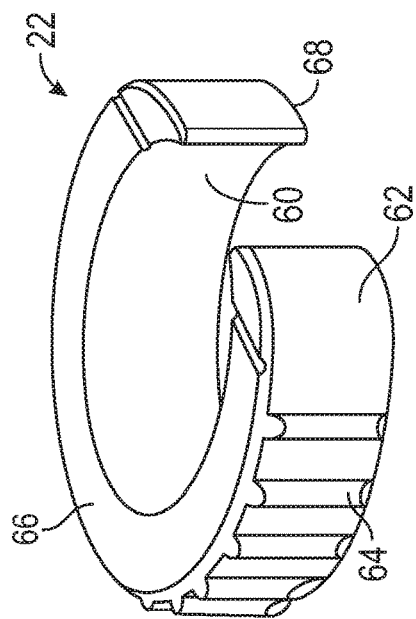
FIG. 3 is a perspective view of a locking element of the tension isolating adjustable adapter of FIG. 1.

The locking element 22 is illustrated in FIGS. 1 and 3 as having a semi-circular or C-shaped cross-section. The locking element 22 has an inner surface 60 and an outer surface 62. The inner surface 60 is provided with a size and shape that allows the locking element 22 to matingly and slidably engage the first groove 48 of the percutaneous device holder 20. In addition, in certain non-limiting embodiments, the outer surface 62 of the locking element 22 is provided with a plurality of protrusions 64 thereon that aid in the positioning, placement, and adjustment of the locking element 22 in its assembly with the percutaneous device holder 20.

While the locking element 22 is illustrated in FIG. 3 as having a substantially semi-circular or C-shape, this configuration will be understood as being for purposes of illustration only. The locking element 22 may be provided with any size/shape, as well as any combination of sizes/ shapes, that may be desired by a person of ordinary skill in the art. Indeed, the locking element 22 may be provided with any size/shape (or combinations of sizes/shapes) that allow the locking element 22 to interact with the percutaneous device 12 and the percutaneous device holder 20 in the manner and function as described or otherwise contemplated herein.

Figure 4:
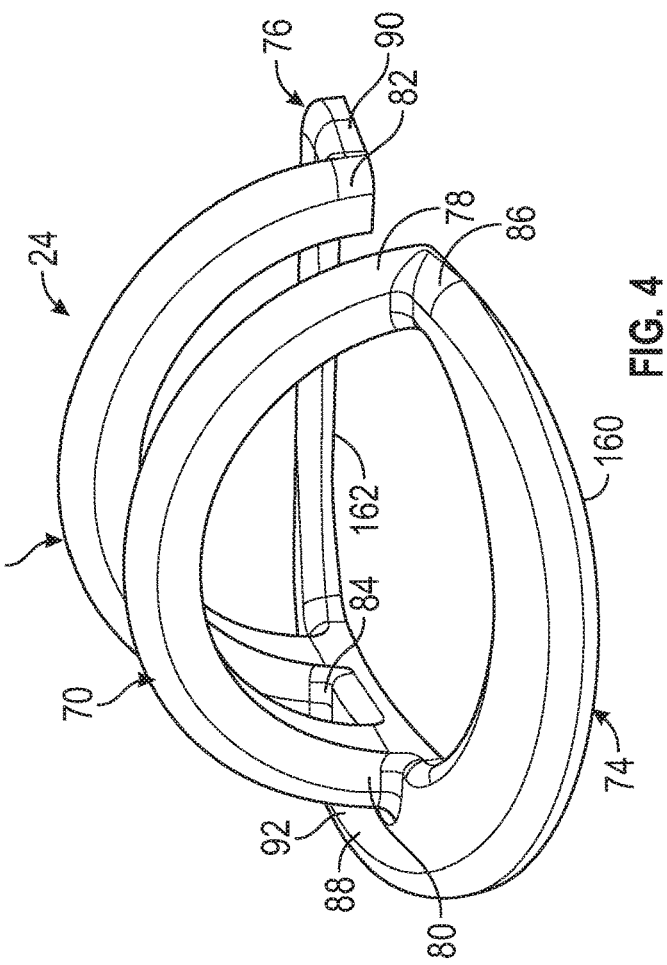
FIG. 4 is a perspective view of a tensioning member of the tension isolating adjustable adapter of FIG. 1.

The tensioning member 24 is designed to be releasably connected or coupled to the percutaneous device holder 20. The tensioning member 24 is illustrated in FIGS. 1 and 4 as having a first guide rail 70, a second guide rail 72, a first tension pad 74, and a second tension pad 76. The first guide rail 70 has a first end 78 and a second end 80, and the second guide rail 72 has a first end 82 and a second end 84. The first tension pad 74 has a first end 86 and a second end 88, and the second tension pad 76 has a first end 90 and a second end 92. The first end 78 of the first guide rail 70 is illustrated as being connected to the first end 86 of the first tension pad 74, and the second end 80 of the first guide rail 70 is illustrated as being connected to the second end 88 of the first tension pad 74. Likewise, first end 82 of the second guide rail 72 is illustrated as being connected to the first end 90 of the second tension pad 76, and the second end 84 of the second guide rail 72 is illustrated as being connected to the second end 92 of the second tension pad 76. In this manner, the first tension pad 74 extends from the first guide rail 70, and the second tension pad 76 extends from the second guide rail 72. However, this configuration of connections between the guide rails and tension pads is for purposes of example only, and it will be understood that any connection configuration can be utilized in accordance with the present disclosure, so long as the tensioning member 24 is capable of functioning in the manner described or otherwise contemplated herein.

The first and second guide rails 70 and 72 are spaced apart from one another in a parallel relationship, and the first and second guide rails 70 and 72 are releasably inserted into opposite sides of the second groove 50 of the percutaneous device holder 20. As described in detail herein after, the first and second tension pads 74 and 76 are each shaped and configured to be disposed about an insertion site of the percutaneous device 12 into a patient's skin. Each of the first and second guide rails 70 and 72 slidably engages opposite sides of the second groove 50 of the percutaneous device holder 20 and allow for adjustment of the first and/or second tension pads 74 and 76 on the patient's skin. In addition, the first and second tension pads 74 and 76 contact the patient's skin with a sufficient amount of pressure so as to maintain the skin disposed between the first and second tension pads 74 and 76 in a substantially taut orientation and thereby distribute any force exerted by the percutaneous device around the area of skin disposed between the first and second tension pads 74 and 76.

While the tensioning member 24 is illustrated in FIGS. 1 and 4 as comprising two guide rails and two tension pads, it will be understood that the tensioning member may only be provided with one guide rail and one tension pad, or more than two guide rail/tension pad combinations. For example (but not by way of limitation), FIG. 15 (which is described in detail herein after) illustrates a tensioning member with a single guide rail and a single tension pad.

Each component of the tension isolating adjustable adapter 10 (i.e., the percutaneous device holder 20, the locking element 22, and the tensioning member 24) may be formed of any material (or combination of materials) that allows the tension isolating adjustable adapter 10 to function in accordance with the present disclosure. For example (but not by way of limitation), each of the components of the tension isolating adjustable adapter 10 may be formed of a material independently selected from metallic, polymeric, and/or biodegradable materials. In addition, each component of the tension isolating adjustable adapter 10 may be integrally formed or may be produced from one or more parts/elements. In addition, each component of the tension isolating adjustable adapter 10 may be substantially rigid, partially flexible, or substantially flexible.

Figure 5:
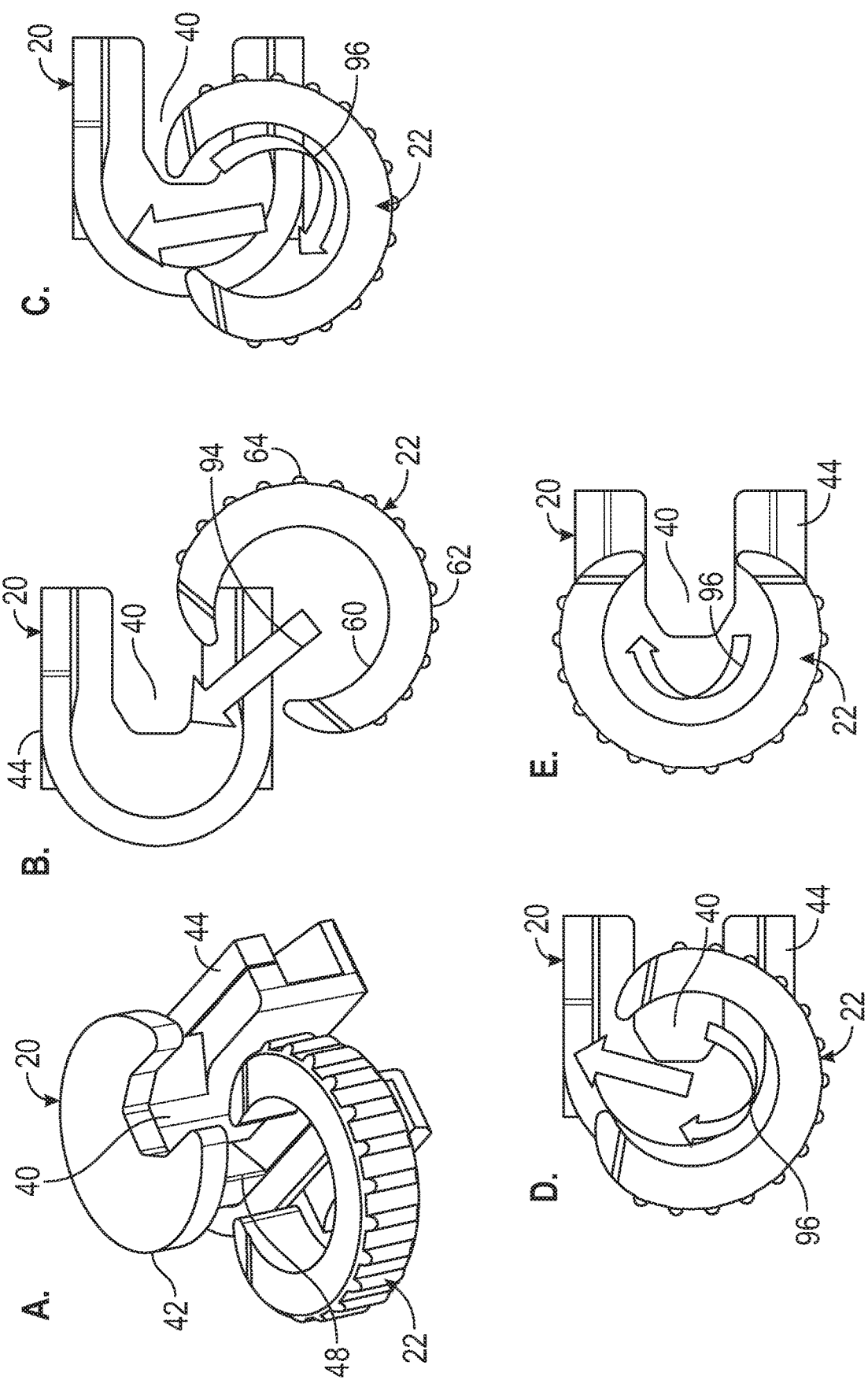
FIG. 5 contains various diagrammatic views demonstrating the assembly of the percutaneous device holder of FIG. 2 with the locking element of FIG. 3.

FIG. 5 illustrates the assembly of the locking element 22 with the percutaneous device holder 20. As shown in Panels (1)-(3), the locking element 22 is slid onto the percutaneous device holder 20 in direction 94 and then twisted in place in direction 96 until the inner surface 60 of the locking element 22 engages the first groove 48 of the percutaneous device holder 20. Panel (5) depicts the assembly of the locking element 22 and percutaneous device holder 20 where the locking element 22 is retained in an open position (i.e., where the recess 40 is not covered by the locking element 22).

Figure 6:
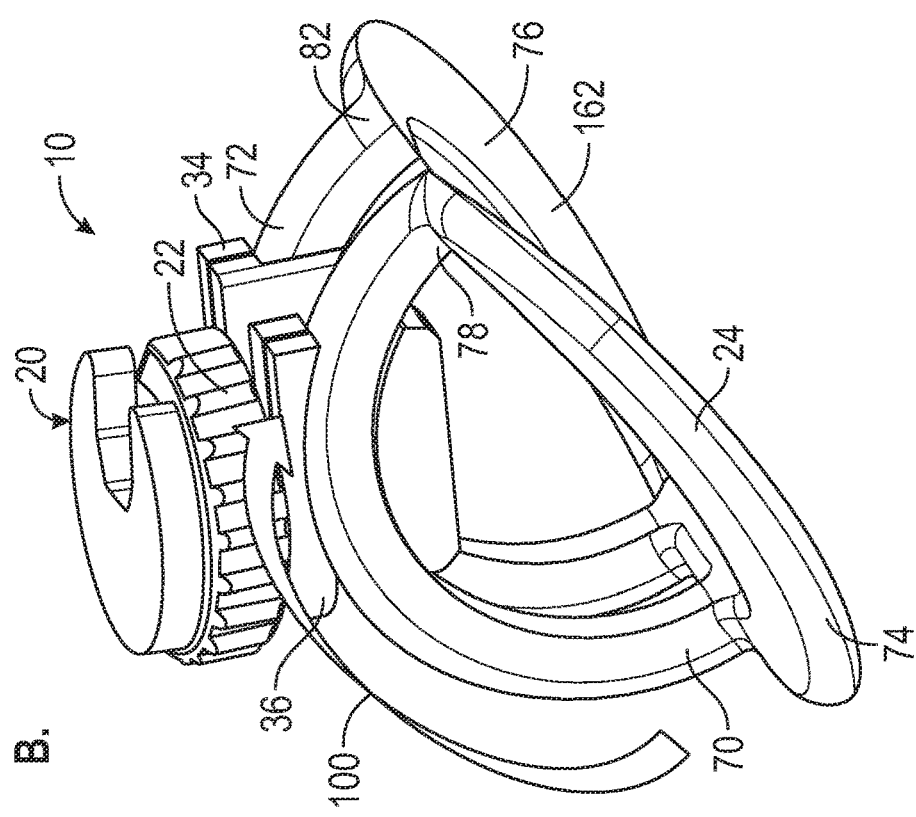
FIG. 6 contains two diagrammatic views demonstrating the assembly of the tension isolating adjustable adapter of FIG. 1, and in particular, the addition of the tensioning member of FIG. 4 to the percutaneous device holder/locking element assembly of FIG. 5.
Figure 6:
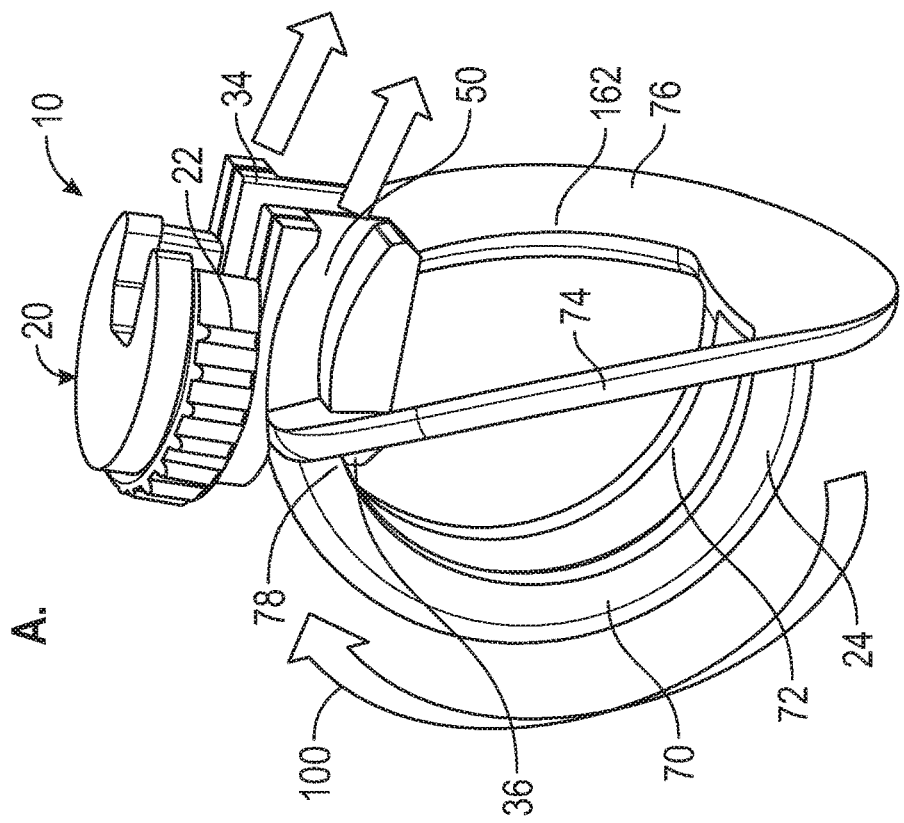

FIG. 6 illustrates the addition of the tensioning member 24 to the locking element 22 and percutaneous device holder 20 of FIG. 5 to form the tension isolating adjustable adapter 10. In this step, the first ends 78 and 82 of the guide rails 70 and 72, respectively, of the tensioning member 24 are each slid through the second groove 50 of the percutaneous device holder 20 from the back end 36 to beyond the front end 34 of the percutaneous device holder 20 in a direction 100. The placement and angle of the tensioning member 24 can also be adjusted in this manner.

Figure 7:
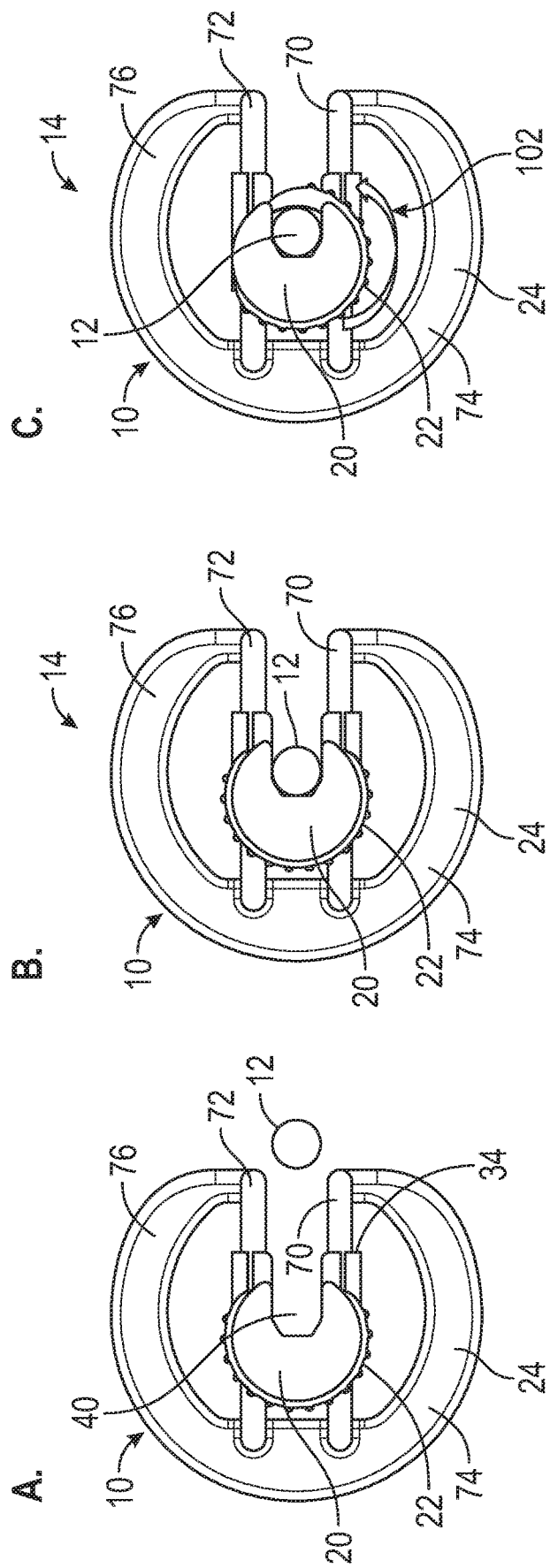
FIG. 7 contains various top planar views demonstrating the placement of the tension isolating adjustable adapter about a percutaneous device and partially securing the adapter thereabout.

FIG. 7 illustrates the attachment of the tension isolating adjustable adapter 10 to a percutaneous device 12, as seen from above. The tension isolating adjustable adapter 10 is slid over the percutaneous device 12 in a manner so that the percutaneous device 12 is inserted through the front end 34 of the percutaneous device holder 20 into the recess 40, as shown in Panels (1) and (2). Then the locking element 22 is moved slightly in a direction 102 to cover at least part or all of the recess 40 and partially secure the tension isolating adjustable adapter 10 in place about the percutaneous device 12. However, the locking element 22 is retained in a partially closed position so that the tension isolating adjustable adapter 10 is still able to slide up and down a length of the percutaneous device 12. In addition, in this partially closed position, the guide rails 70 and 72 are still able to rotate or rock back and forth within the second groove 50 of the percutaneous device holder 20 and thereby allow for adjustment of the tension pads 74 and 76 as needed.

Figure 8:
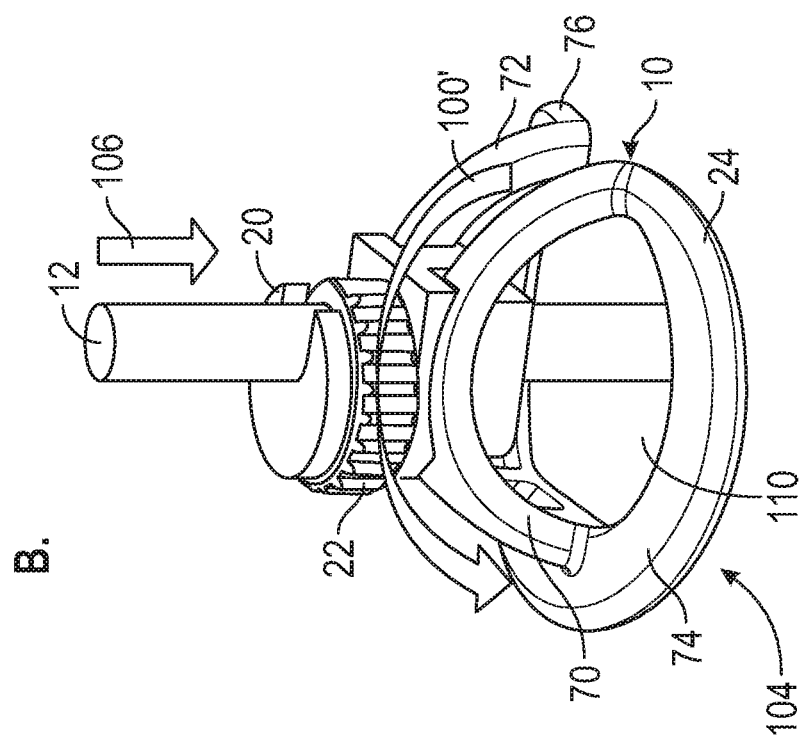
FIG. 8 contains two diagrammatic views demonstrating the placement and adjustment of the tension isolating adjustable adapter about an externally extending portion of a percutaneous device that is fixated within a body of a patient. The tension isolating adjustable adapter is disposed about the externally extending portion of the percutaneous device and then adjusted so that the tensioning member contacts the patient's skin with a sufficient amount of pressure so as to maintain the skin disposed between the two tension pads of the tensioning member in a substantially taut orientation and thereby distribute any force exerted by the percutaneous device around the area of skin disposed between the two tension pads.
Figure 8:
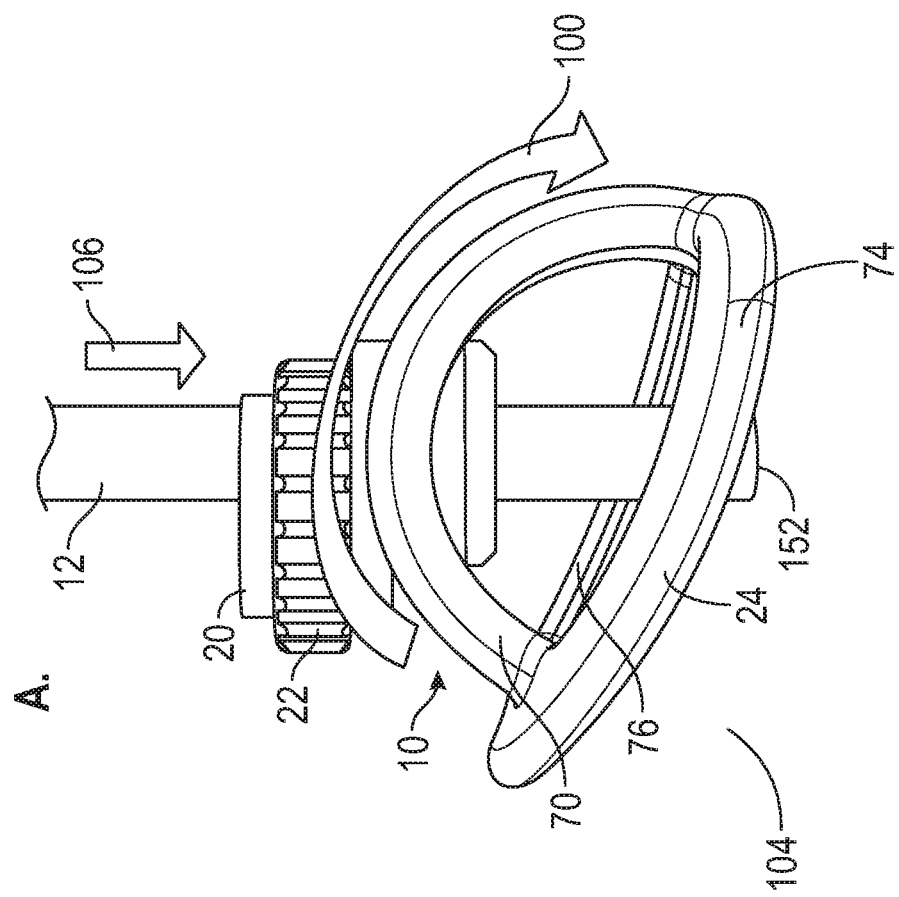

FIG. 8 illustrates the placement and adjustment of the tension isolating adjustable adapter 10 on the patient's skin 104 that surrounds the percutaneous device 12. First, the tension isolating adjustable adapter 10 is slid down the percutaneous device 12 in a direction 106 until at least a portion of the tension pads 74 and 76 contact the patient's skin 104. Then the tensioning member 24 is adjusted by moving the guide rails 70 and 72 back and forth (for example, in direction 100 or 100') until the best skin coverage is obtained such that the tension pads 74 and 76 contact the patient's skin 104 with a sufficient amount of pressure so as to maintain an area 110 of the patient's skin 104 disposed between the two tension pads 74 and 76 of the tensioning member 24 in a substantially taut orientation and thereby distribute any force exerted by the percutaneous device 12 around the area 110 of skin 104 disposed between the two tension pads 74 and 76.

Figure 9:
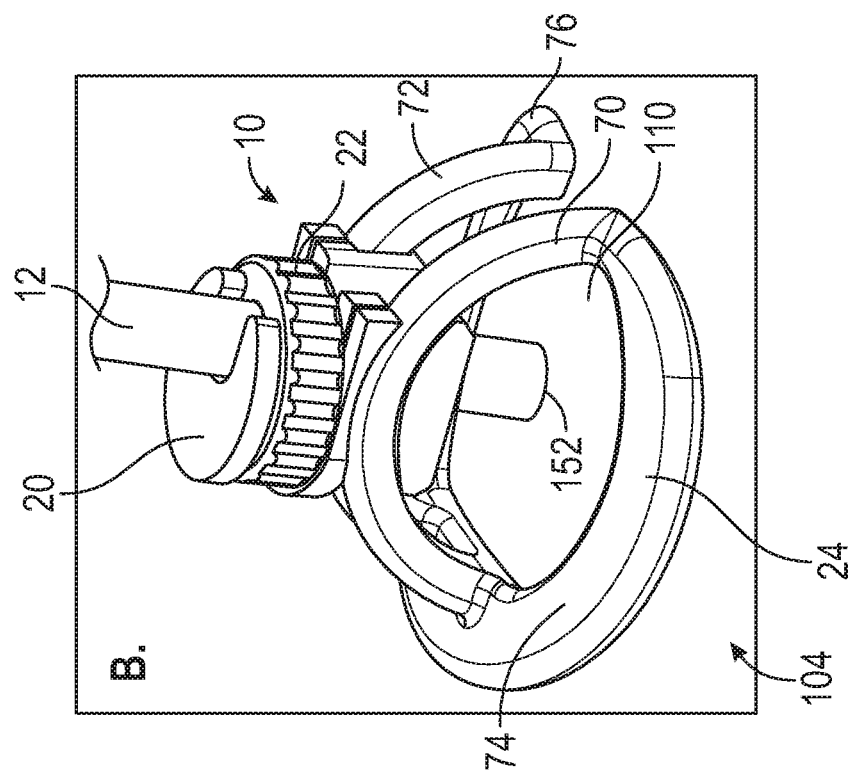
FIG. 9 contains two diagrammatic view demonstrating the securing of the tension isolating adjustable adapter in position about the percutaneous device.
Figure 9:
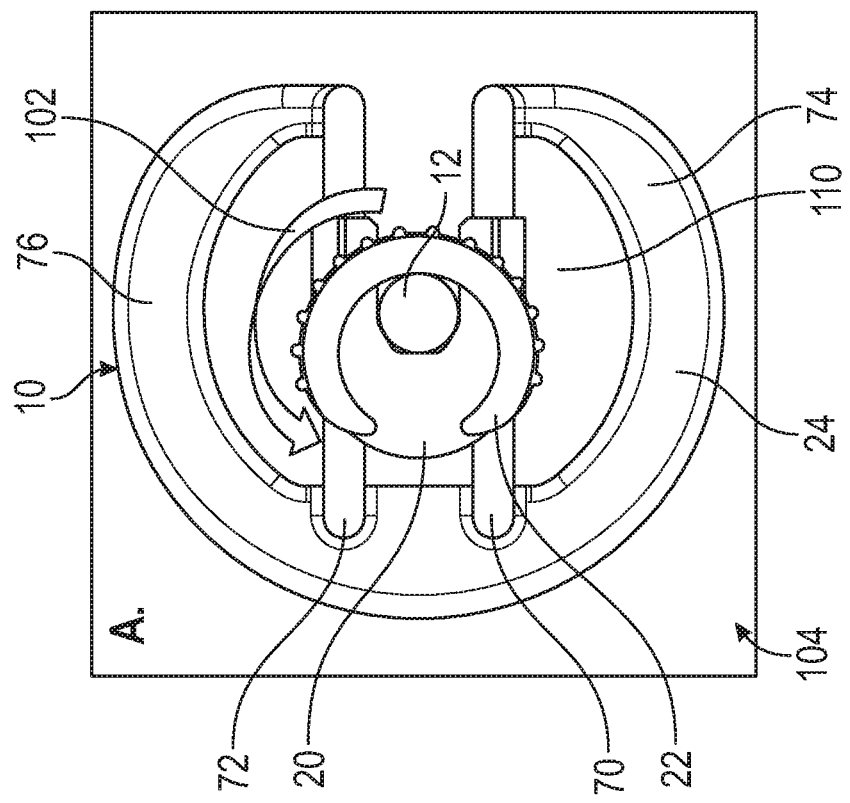

Then, as shown in FIG. 9, the locking element 22 is rotated further in the direction 102 to secure the tension isolating adjustable adapter 10 at the desired placement along the length of the percutaneous device 12 and to secure the tension pads 74 and 76 on the patient's skin 104 such that the sufficient amount of pressure to maintain the area 110 of skin 104 in a substantially taut orientation in the manner described herein above. When the locking element 22 is in this fully closed position, the guide rails 70 and 72 are locked in place to prevent movement of the tension pads 74 and 76.

While the tension pads 74 and 76 must place a sufficient amount of pressure on the patient's skin 104 to obtain tautness of the area 110 of skin 104 disposed therebetween, this amount of pressure should generally also be light enough that there is no impingement of the tissue underneath the skin 104 disposed under the tension pads 74 and 76. To further reduce the possibility of impingement, in certain non-limiting embodiments, the tension pads 74 and 76 may be formed of a flexible or semi-flexible material.

Figure 10:
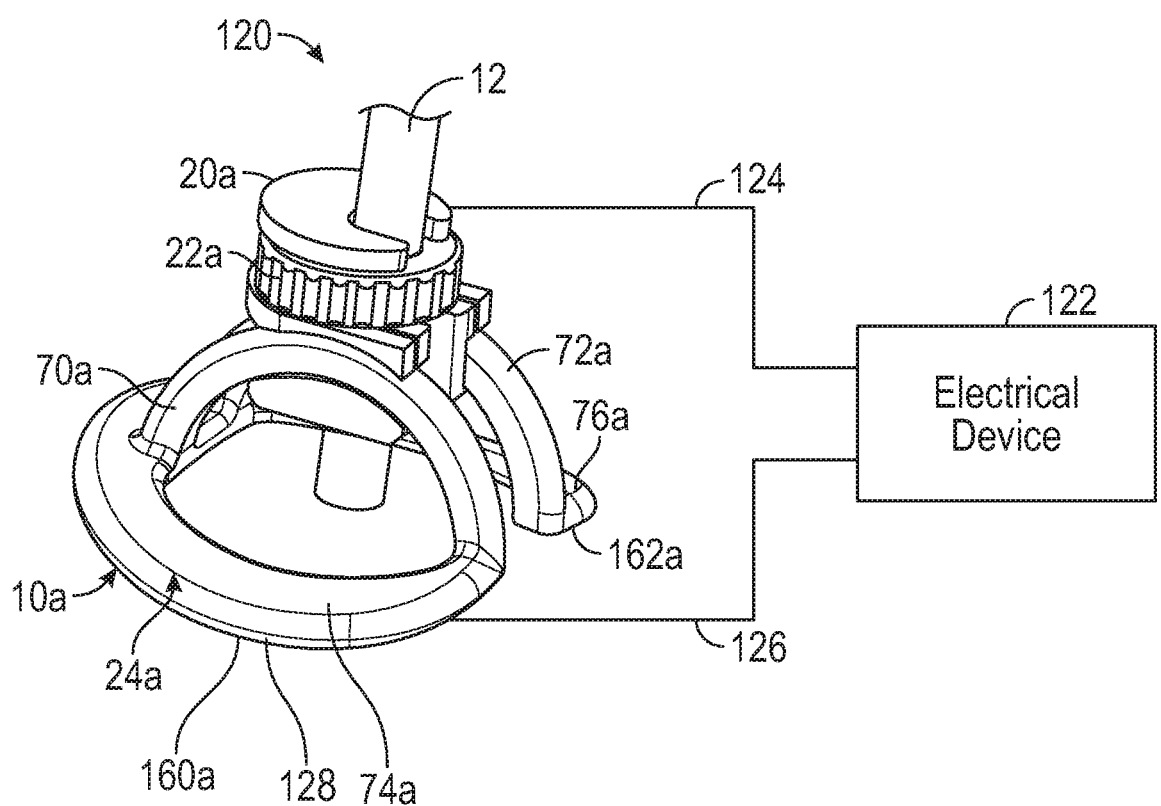
FIG. 10 is a perspective view of another non-limiting embodiment of a system constructed in accordance with the present disclosure. This embodiment includes a tension isolating adjustable adapter, a percutaneous device, and an electrical device for monitoring, preventing, and/or treating implant infections.

The tension isolating adjustable adapters 10 of the present disclosure may be utilized with any other apparatus/devices for use with percutaneous devices that are known in the art or disclosed or otherwise contemplated herein. For example (but not by way of limitation), FIG. 10 illustrates a system 120 that includes a tension isolating adjustable adapter 10*a* in combination with an electrical device 122 for monitoring, preventing, and/or treating implant infections (as described in detail in U.S. Ser. No. 16/999,597, incorporated supra). The tension isolating adjustable adapter 10*a* is identical to the tension isolating adjustable adapter 10 of FIGS. 1-9 and described in detail herein above, except that the tension isolating adjustable adapter 10*a* further includes an electrode element 128 (such as, but not limited to, a metal pad or ring) attached to a lower surface 160*a* and/or 162*a* of a first tension pad 74*a* and/or a second tension pad 76*a*, respectively, of a tensioning member 24*a* of the tension isolating adjustable adapter 10*a*. In addition, either the percutaneous device 12 is conductive, or a percutaneous device holder 20*a* of the tension isolating adjustable adapter 10*a* is provided with an electrode element thereon or therein. The system 120 further includes a first electrical lead 124 that connects the electrical device 122 to either the conductive percutaneous device 12 or an electrode element of the percutaneous device holder 20*a*, and a second electrical lead 126 that connects the electrical device 122 to the electrode element 128 of the tensioning member 24*a*.

Figure 11:
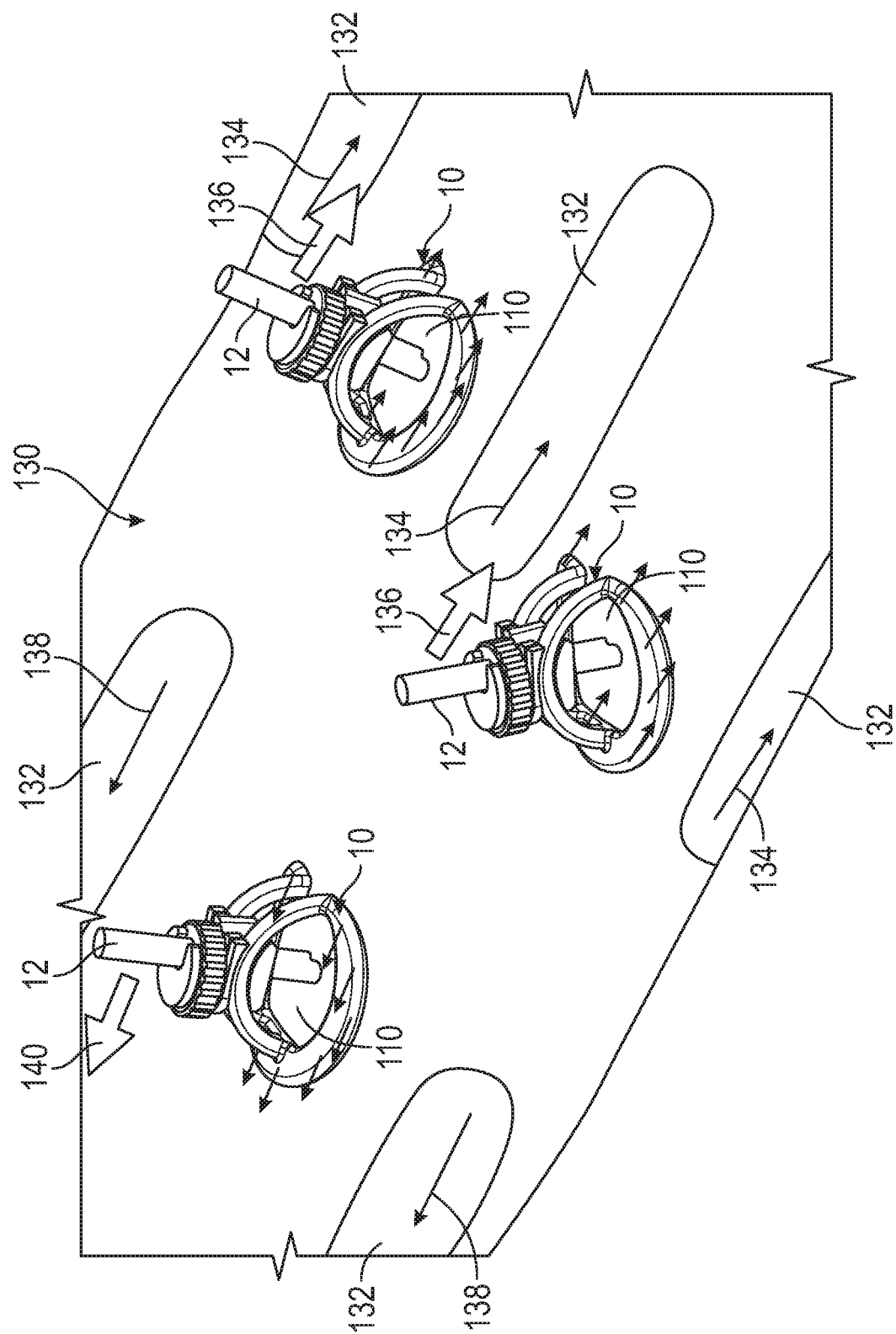
FIG. 11 is a perspective view of another non-limiting embodiment of a system constructed in accordance with the present disclosure. This embodiment includes a plurality of tension isolating adjustable adapters, each disposed about a percutaneous device, and a plurality of elastically deformable membranes.

Alternatively (and/or in addition thereto), FIG. 11 illustrates a system 130 that includes a plurality of tension isolating adjustable adapters 10 in combination with a plurality of elastically deformable membranes 132, as described in detail in U.S. Ser. No. 16/590,810, incorporated supra. In this instance, a force (such as, but not limited to, a distraction force) is applied in a direction 136 to the percutaneous device 12 to which certain tension isolating adjustable adapters 10 are attached, whereas a force (such as, but not limited to, a distraction force) is applied in an opposite direction 140 to another percutaneous device 12 to which another tension isolating adjustable adapter 10 is attached. In this manner, the distraction forces from the percutaneous devices 12 are rigidly transmitted to the tension pads of the tension isolating adjustable adapters 10, thus bypassing the area 110 of skin disposed between the first and second tension pads. As a result, the area 110 of skin disposed between the first and second tension pads travels with the tension isolating adjustable adapters, and the incision/insertion site is protected from tension created by the percutaneous devices 12.

In a similar manner, five segments of elastically deformable membrane 132 are applied to the skin by any of the methods described in the '810 application. In addition, three segments of elastically deformable membrane 132 are being caused to move in a direction 134, while two segments of elastically deformable membrane 132 are being caused to move in an opposite direction 138. The expansion force from the elastically deformable membranes aids in stretching the entire skin and underlying tissue in cooperation with the bone distraction being performed by the percutaneous devices.

Figure 12:
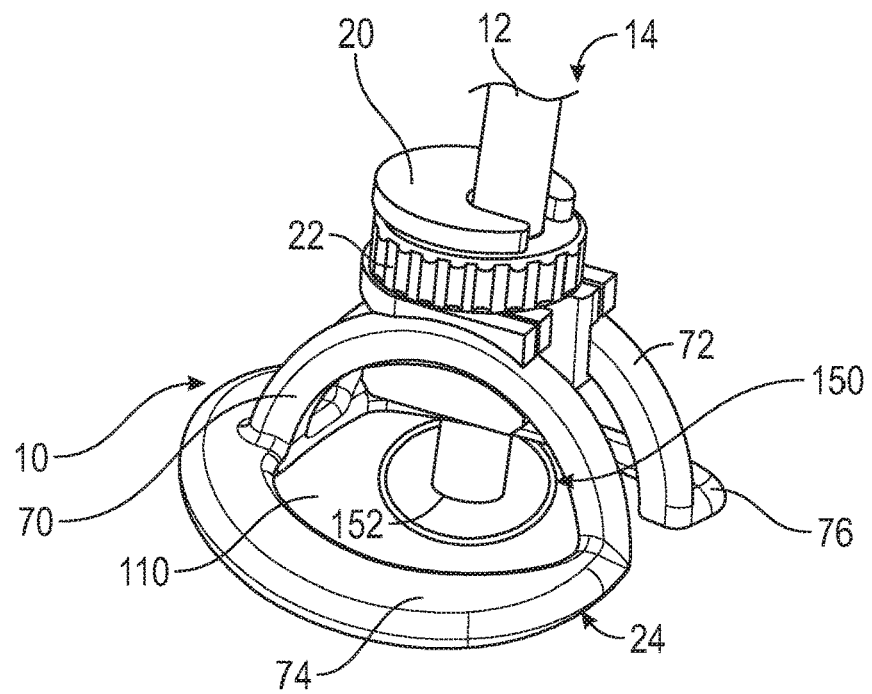
FIG. 12 is a perspective view of a tension isolating adjustable adapter/percutaneous device system disposed about a patient's skin, illustrating the ease of access to the percutaneous device insertion site for wound care.

The tension isolating adjustable adapters of the present disclosure are provided with various design features that overcome various disadvantages and defects of the prior art. For example, as shown in FIG. 12, the design of the tensioning member 24 may contain openings that allow for easy access to an area 150 of skin immediately surrounding the insertion site 152 of the percutaneous device 12 for wound care, such as (but not limited to) the application of antimicrobial or other infection prevention agents. Alternatively (and/or in addition thereto), the locking element 22 can be moved to the partially open position, and the tension isolating adjustable adapter 10 moved up the length of the percutaneous device 12 (or removed altogether) to further aid in access to the insertion site area 150.

Figure 13:
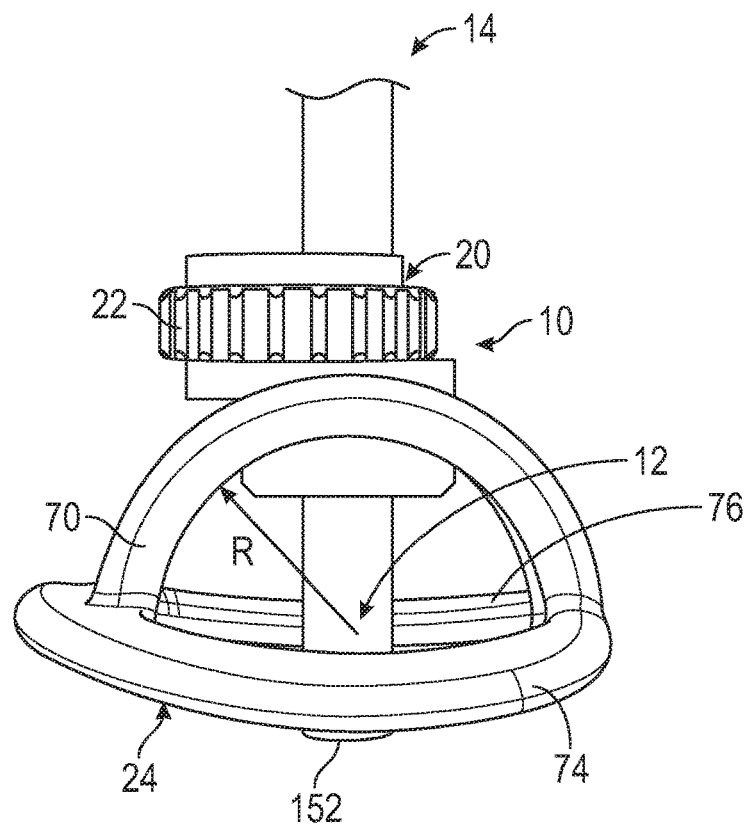
FIG. 13 is a perspective view of a tension isolating adjustable adapter/percutaneous device system, illustrating an optional self-centering aspect of the tensioning member.

FIG. 13 illustrates an optional self-centering aspect for the tensioning member 24 of the tension isolating adjustable adapter pad 10. In certain non-limiting embodiments, the center of rotation for the tensioning member 24 may be located at the insertion site 152 of the percutaneous device 12. The purpose of this positioning is to maintain the area 110 of skin between the two tension pads 74 and 76 centered around the percutaneous device 12, regardless of a tilt angle of the tension pads 74 and 76. However, it is to be understood that this is simply one non-limiting embodiment of the present disclosure, and the tensioning member 24 may be designed so that the percutaneous device 12 is centered or off-centered between the two tension pads 74 and 76.

Figure 14:
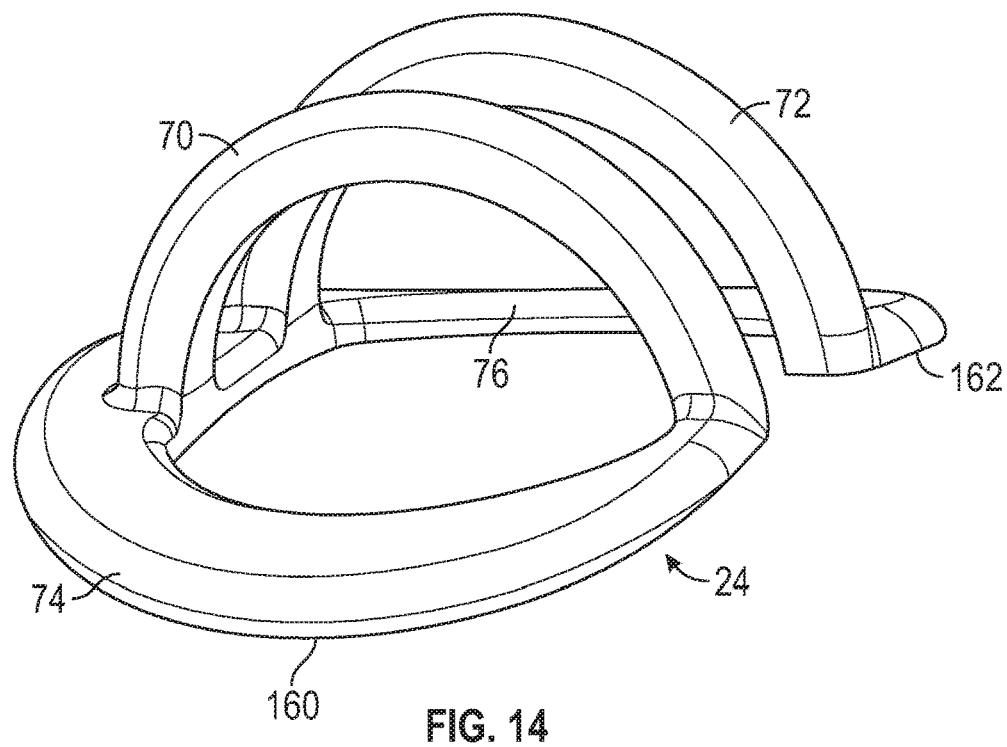
FIG. 14 is a perspective view of another non-limiting embodiment of a tensioning member constructed in accordance with the present disclosure, wherein the two tension pads of the tensioning member are substantially anatomically-shaped.

FIG. 14 illustrates additional optional design features for the tensioning member 24. First, the tension pads 74 and 76 may be anatomically shaped. In certain non-limiting embodiments, the tension pads 74 and 76 may be replaceable and include lower surfaces 160 and 162 that are formed to accommodate various skin shapes and sizes. In addition, the lower surfaces 160 and 162 of the tension pads 74 and 76, respectively, may be provided with a slip resistant material, an adhesive material, a tacky jelly-like material, or other types of material (or combinations thereof) that aid in maintaining the stability of the area 110 of skin disposed between the two tension pads 74 and 76 and thus reduce the amount of pressure required to maintain the taut orientation of the area 110 of skin.

Figure 15:
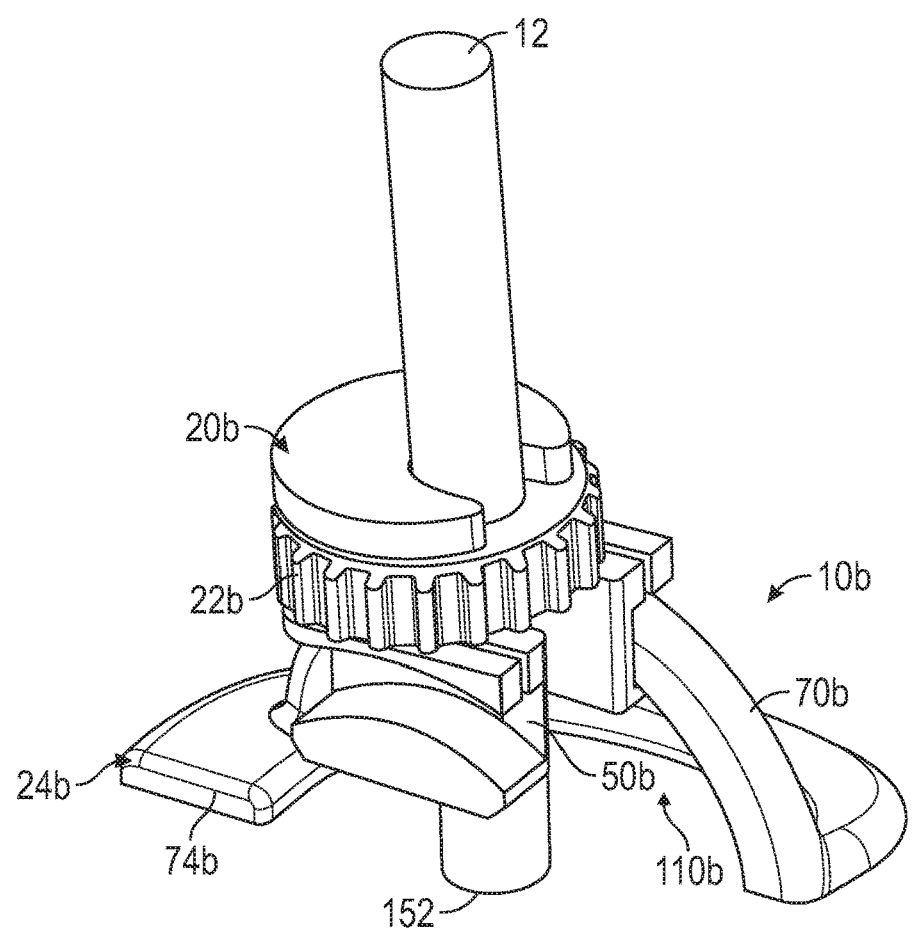
FIG. 15 is a perspective view of a tension isolating adjustable adapter/percutaneous device system that utilizes another non-limiting embodiment of a tension isolating adjustable adapter constructed in accordance with the present disclosure. In this embodiment, the tensioning member of the adapter includes only one tension pad.

FIG. 15 illustrates another non-limiting embodiment of a tension isolating adjustable adapter pad 10*b* constructed in accordance with the present disclosure. The tension isolating adjustable adapter pad 10*b* is similar to the tension isolating adjustable adapter pads 10 and 10*a*, except that a tensioning member 24*b* of the adapter 10*b* has a single guide rail 70*b* and a single tension pad 74*b* extending from the guide rail 70*b*. The guide rail 70*b* is releasably inserted into a second groove 50*b* of a percutaneous device holder 20*b*, and the tension pad 74*b* is shaped and configured to be disposed about an insertion site 152 of the percutaneous device 12 into a patient's skin. The guide rail 70*b* slidably engages the second groove 50*b* of the percutaneous device holder 20*b* in the same manner as described above, which allows for adjustment of the tension pad 74*b* on the patient's skin. In addition, the tension pad 74*b* contacts the patient's skin with a sufficient amount of pressure so as to maintain an area 110*b* of skin disposed between inner edges of the tension pad 74*b* and the percutaneous device insertion site 152 in a substantially taut orientation and thereby distribute any force exerted by the percutaneous device 12 around the area 110*b* of skin disposed between the percutaneous device insertion site 152 and the tension pad 74*b*.

The use of a single tension pad in the manner shown in FIG. 15 will accommodate various different positionings and placements of percutaneous devices. For example (but not by way of limitation), multiple percutaneous devices may be placed in close proximity to one another such that there is not enough room to add a tension isolating adjustable adapter containing two tension pads about each percutaneous device. Alternatively (and/or in addition thereto), the patient's anatomy may not allow for the presence of a tension isolating adjustable adapter containing two tension pads.

A tensioning member 24*b* may be produced in the configuration shown in FIG. 15. Alternatively, the tensioning member 24 of FIG. 4 may be provided with score lines or perforations (or other similar separation device, such as, but not limited to, markings or embossings) at the connection between the second end 88 of the first tension pad 74 and the second end 92 of the second tension pad 76. These separation devices allow for separation of a single guide rail and tension pad from the tensioning member 24 to produce the tensioning member 24*b*.

Figure 16:
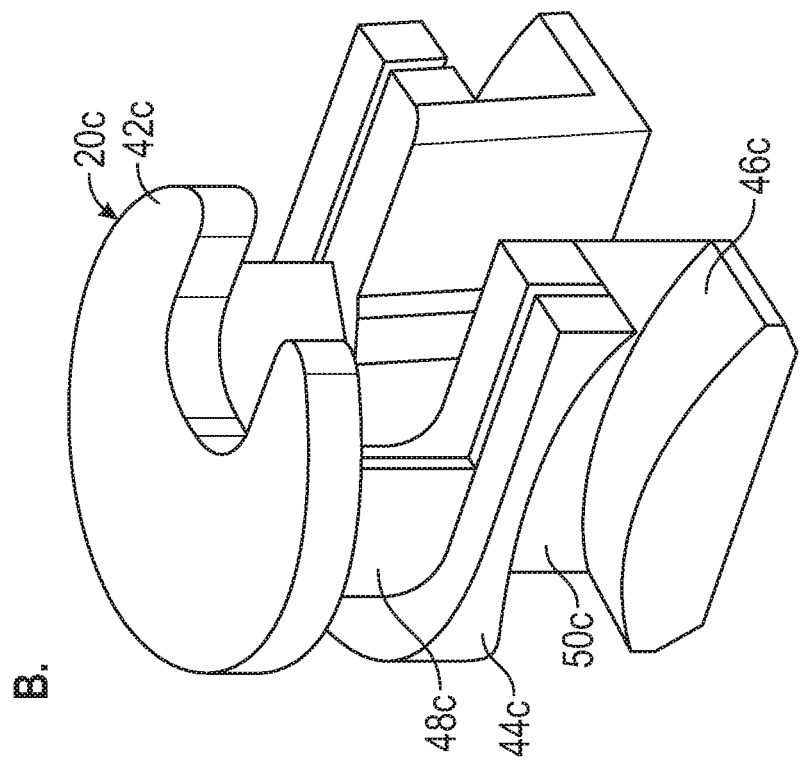
FIG. 16 contains perspective views of a locking element (left) and percutaneous device holder (right) of another non-limiting embodiment of a tension isolating adjustable adapter constructed in accordance with the present disclosure.
Figure 16:
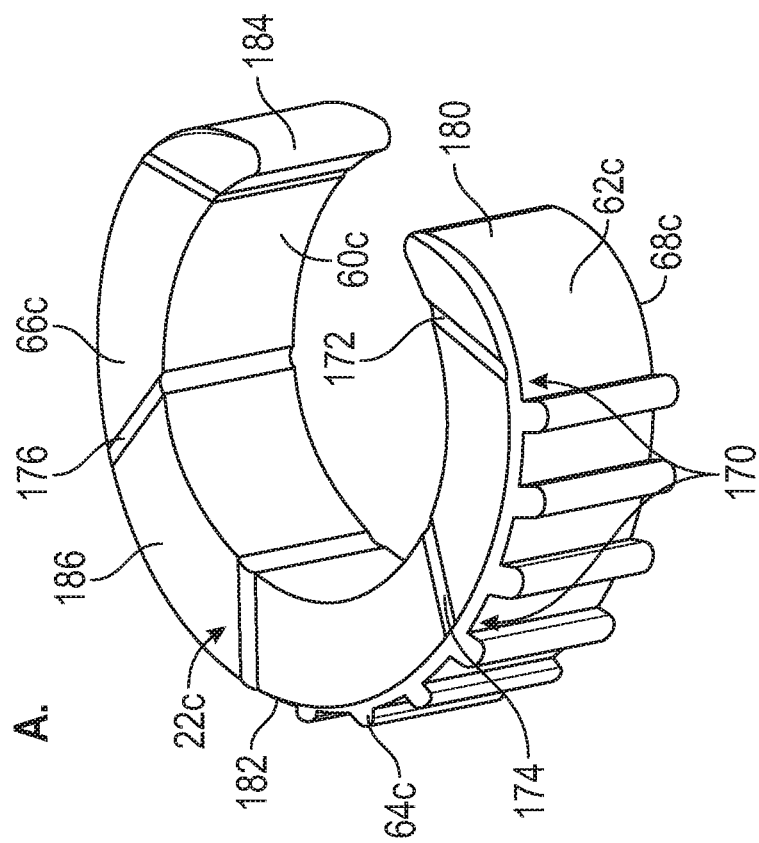

Another design feature that may be present in the percutaneous device holder and/or locking element of the tension isolating adjustable adapters in certain non-limiting embodiments of the present disclosure is the ability to retain and/or lock the adapter in multiple positions. For example (but not by way of limitation), the left panel of FIG. 16 illustrates a multi-position retaining and locking element 22*c* that is similar to the locking element 22, except as described herein. The locking element 22*c* contains multiple retaining/locking elements (such as, but not limited to, grooves, slots, or protrusions) in one, two, three, or more orientations. For example (but not by way of limitation), the locking element 22*c* has an inner surface 60*c*, an outer surface 62*c*, an upper surface 66*c*, and a lower surface 68*c*, and the multiple retaining/locking elements 170 may be disposed on a portion of one or more of the surfaces 60*c*, 62*c*, 66*c*, and 68*c*. In addition, the upper surface 66*c* and/or lower surface 68*c* may be absent any retaining/locking elements thereon, and as such, the surface 66*c* and/or 68*c* may be substantially flat/smooth.

For example (but not by way of limitation), FIG. 16 depicts the locking element 22*c* as containing a first slot or groove (or set of slots/grooves) 172 formed in at least the upper surface 66*c* thereof in close proximity to a first end 180 of the locking element 22*c*, a second slot or groove (or set of slots/grooves) 174 formed in at least the upper surface 66*c* thereof at a position proximal to a back edge 182 of the locking element 22*c*, and a third slot or groove (or set of slots/grooves) 176 formed in at least the upper surface 66*c* thereof at a position between the back edge 182 and a second end 184 of the locking element 22*c*. In addition, the locking element 22*c* may further be provided with a flattened portion 186 on at least the upper surface 66*c* thereof at a position in between the second slot/groove 174 and the third slot/groove 176; the flattened portion 186 may also be present on the lower surface 68*c* of the locking element 22*c*.

The multiple retaining/locking elements 170 (such as, but not limited to, the slots/grooves 172, 174, and 176) frictionally contact a percutaneous device holder and/or tensioning member and function to provide a cam feature to the locking element 22*c* for providing a tighter connection between the locking element 22*c* and a corresponding percutaneous device holder and/or tensioning member utilized therewith. In addition, the cam feature may allow a tension isolating adjustable adapter 10*c* containing same to move up and down the length of the percutaneous device 12, or the cam feature may hold the tension isolating adjustable adapter 10*c* in an axial orientation.

The right panel of FIG. 16 illustrates a percutaneous device holder 20*c* that may be utilized with any of the locking and tensioning members described or otherwise contemplated herein to form a tension isolating adjustable adapter 10*c* in accordance with the present disclosure. The percutaneous device holder 20*c* may be formed of a flexible, springy, elastic, and/or resilient material, or the percutaneous device holder 20*c* may be provided with springs and/or protrusions formed therewithin.

Figure 17:
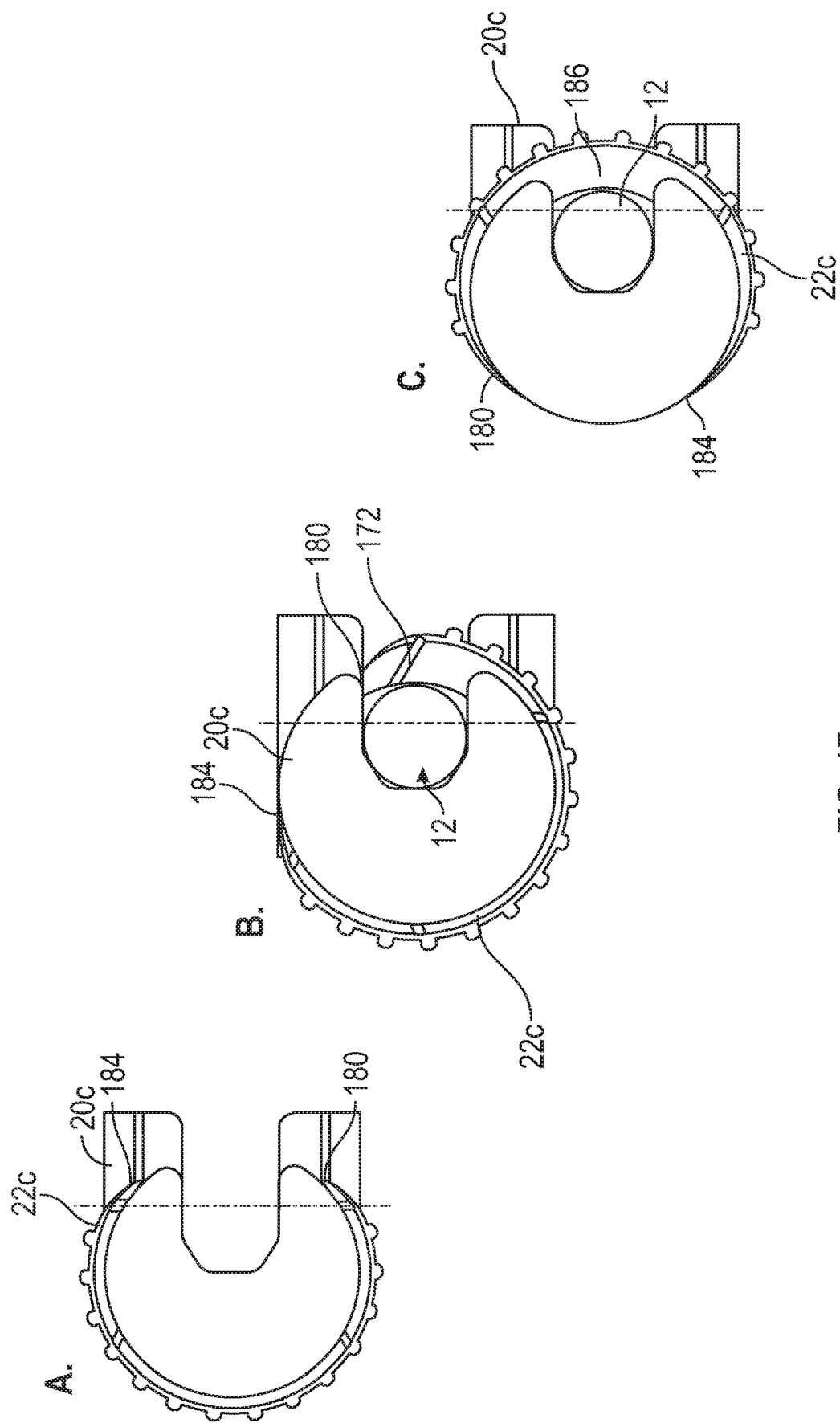
FIG. 17 contains diagrammatic views of an assembly of the percutaneous device holder and locking element of FIG. 16 about a percutaneous device.

FIG. 17 illustrates the positioning and retainment of a tension isolating adjustable adapter (formed from the percutaneous device holder 20*c* and the locking element 22*c* of FIG. 16) about a percutaneous device 12 that is inserted through a patient's skin and fixated within the body. In this non-limiting embodiment, the slot/groove 172 of the locking element 22*c* is snapped over spring protrusions on the percutaneous device holder 20*c* within or adjacent to the first groove 48*c* thereof. The first slot/groove 172 maintains the locking element 22*c* in an open position while the tension isolating adjustable adapter 10*c* containing the percutaneous device holder 20*c* and the locking element 22*c* is placed over an external end of the percutaneous device 12. Once the percutaneous device 12 is in place, the locking element 22*c* is rotated until the second slot/groove 174 is snapped over spring protrusions on the percutaneous device holder 20*c* within or adjacent to the first groove 48*c* thereof. This maintains the locking element 22*c* in a partially closed position, which allows the adapter 10*c* containing same to be adjusted along a length of the percutaneous device 12 without the need for manually holding the adapter 10*c* about the percutaneous device 12. The third slot/groove 176 serves the same function as the second slot/groove 174, but in the opposite direction.

Once the tension isolating adjustable adapter 10*c* reaches a desired placement with respect to the percutaneous device 12 and the patient's skin, the locking element 22*c* is again rotated until the flattened portion 186 on the upper surface 66*c* of the locking element 22*c* locks the adapter 10*c* in place with respect to the percutaneous device 12. The flattened portion 186 may also form a slightly expanded portion on the inner surface 60*c* of the locking element 22*c* that frictionally contacts the percutaneous device 12 and applies sufficient pressure thereto to secure the adapter 10*c* about the percutaneous device 12 and lock the adapter 10*c* in place at a particular position along the length of the percutaneous device 12. Likewise, the flattened portion 186 may also be present on the lower surface 68*c* of the locking element 22*c* and frictionally engage the second flange 44*c* of the percutaneous device holder 20*c*. This frictional engagement activates springs associated with the percutaneous device holder 20*c*, which act like brake pads to lock the guide rail(s) of a tensioning member of the adapter 10*c* in place and thus prevent movement of the tension pad(s) of the tensioning member after initial placement and positioning upon the patient's skin.

While certain embodiments shown in the Drawings and described herein illustrate the devices, systems, and methods of the present disclosure being utilized with external fixation in combination with distraction osteogenesis, it will be understood that the systems and methods disclosed herein are not limited to use with distraction osteogenesis. That is, as described herein above, pin tracks can be formed simply as the result of patient movement when an external fixation system is in place, or even as a result of gravity or slight movement/adjustment of the external fixation system. Therefore, the scope of the present disclosure explicitly includes devices, systems, and methods that can be utilized with any external fixation mechanisms known in the art or otherwise contemplated herein where pin tracks can potentially be formed and, as such, are at risk of infection.

Thus, in accordance with the present disclosure, there have been provided devices, assemblies, and kits, as well as methods of producing and using same, which fully satisfy the objectives and advantages set forth hereinabove. Although the present disclosure has been described in conjunction with the specific drawings, experimentation, results, and language set forth hereinabove, it is evident that many alternatives, modifications, and variations will be apparent to those skilled in the art. Accordingly, it is intended to embrace all such alternatives, modifications, and variations that fall within the spirit and broad scope of the present disclosure.

What is claimed is:

1. A tension isolating adjustable adapter for use with a percutaneous device, the adapter comprising:
   a percutaneous device holder, the percutaneous device holder having a recess sized and shaped to receive a portion of a percutaneous device, the percutaneous device holder further comprising a first groove and a second groove;
   a tensioning member releasably coupled to the percutaneous device holder, the tensioning member having at least one guide rail and at least one tension pad coupled to the guide rail, the at least one guide rail being releasably inserted into the second groove of the percutaneous device holder, wherein the at least one tension pad is shaped and configured to be disposed about an insertion site of the percutaneous device, and wherein the at least one guide rail engages the second groove of the percutaneous device holder in a manner that allows for adjustment of the at least one tension pad; and
   a locking element coupled to the first groove of the percutaneous device holder, wherein the locking element is shaped and configured to secure the percutaneous device holder to the percutaneous device.

2. The tension isolating adjustable adapter of claim 1, wherein the at least one tension pad of the tensioning member is designed to contact the patient's skin with a sufficient amount of pressure so as to maintain the skin disposed between the at least one tension pad and the percutaneous device insertion site in a substantially taut orientation and thereby distribute any force exerted by the percutaneous device around the area of skin disposed between the percutaneous device insertion site and the at least one tension pad.

3. The tension isolating adjustable adapter of claim 1, wherein the at least one guide rail comprises a first guide rail and a second guide rail, and wherein the at least one tension pad comprises a first tension pad and a second tension pad, wherein the first tension pad is coupled to the first guide rail and the second tension pad is coupled to the second guide rail, and wherein the first and second guide rails are spaced apart from one another in a parallel relationship, the first and second guide rails being releasably inserted into opposite sides of the second groove of the percutaneous device holder, wherein the first and second tension pads are shaped and configured to be disposed about the percutaneous device's insertion site in the patient's skin, wherein each of the first and second guide rails engages the second groove of the percutaneous device holder and allows for adjustment of the first and second tension pads.

4. The tension isolating adjustable adapter of claim 3, wherein the first and second tension pads are designed to contact the patient's skin with a sufficient amount of pressure so as to maintain the skin disposed between the first and second tension pads in a substantially taut orientation and thereby distribute any force exerted by the percutaneous device around the area of skin disposed between the first and second tension pads.

5. The tension isolating adjustable adapter of claim 1, wherein the locking element engages the at least one guide rail of the tensioning member and secures the tensioning member in position with respect to the percutaneous device holder.

6. The tension isolating adjustable adapter of claim 1, wherein the at least one tension pad is adjustable to a shape of the patient's skin surface.

7. The tension isolating adjustable adapter of claim 1, wherein the at least one tension pad is substantially anatomically-shaped.

8. The tension isolating adjustable adapter of claim 1, wherein the at least one tension pad is adjustable to an insertion angle of the percutaneous device.

9. The tension isolating adjustable adapter of claim 1, wherein the tension isolating adjustable adapter is releasably securable to the percutaneous device.

10. The tension isolating adjustable adapter of claim 1, wherein the first and second grooves of the percutaneous device holder are each formed on an outer surface of the percutaneous device holder.

11. The tension isolating adjustable adapter of claim 1, wherein at least one of:
    the locking element slidably engages the first groove of the percutaneous device holder; or
    the at least one guide rail of the tensioning member slidably engages the second groove of the percutaneous device holder.

12. A kit, comprising:
    the tension isolating adjustable adapter of claim 1; and
    at least one percutaneous device.

13. The kit of claim 12, further comprising at least one of:
    (i) at least one segment of elastically deformable membrane, wherein the membrane has a bonding material attached to at least a portion of a surface thereof for connecting the membrane to a patient's skin; or
    (ii) an electrical device, comprising:
        a housing;
        a power source configured to supply electrical power to a conductive percutaneous implant in a circuit including the conductive percutaneous implant and tissue of a patient adjacent to the conductive percutaneous implant;
        an electrical sensor configured to generate a signal indicative of at least one electrical parameter of the circuit; and
        at least one data processing system having one or more processors configured to receive the signal and analyze the signal to determine at least one of a presence or change of infection of the tissue, and pass a control signal to the power source to vary the electrical power responsive to determining at least one of the presence or change of infection of the tissue.

14. A system, comprising:
the tension isolating adjustable adapter of claim 1; and
at least one percutaneous device.

15. A method, comprising the steps of:
(A) connecting a tension isolating adjustable adapter to a portion of a percutaneous device, inserting a portion of the percutaneous device through a skin of a patient, and fixating the inserted portion of the percutaneous device within a body of the patient, whereby the portion of the percutaneous device to which the tension isolating adjustable adapter is connected extends above the patient's skin, and wherein the tension isolating adjustable adapter comprises:
a percutaneous device holder having a recess in which a portion of the percutaneous device is received, and wherein the percutaneous device holder further comprises a first groove and a second groove;
a tensioning member releasably coupled to the percutaneous device holder, the tensioning member having at least one guide rail and at least one tension pad coupled to the guide rail, the at least one guide rail being releasably inserted into the second groove of the percutaneous device holder, wherein the at least one tension pad is disposed about an insertion site of the percutaneous device, and wherein the at least one guide rail engages the second groove of the percutaneous device holder in a manner that allows for adjustment of the at least one tension pad; and
a locking element coupled to the first groove of the percutaneous device holder, wherein the locking element secures the percutaneous device holder to the percutaneous device;
(B) adjusting the tension isolating adjustable adapter along the length of the percutaneous device until the at least one tension pad of the tension isolating adjustable adapter contacts the skin of the patient; and
(C) adjusting the at least one tension pad until the at least one tension pad contacts the patient's skin with a sufficient amount of pressure so as to maintain the skin disposed between the insertion site of the percutaneous device and the at least one tension pad in a substantially taut orientation and thereby distribute any force exerted by the percutaneous device around the area of skin disposed between the percutaneous device insertion site and the at least one tension pad.

16. The method of claim 15, further comprising the step of:
adjusting a locking element of the tension isolating adjustable adapter to secure the tension isolating adjustable adapter in position about the percutaneous device, thereby maintaining the sufficient amount of pressure exerted by the at least one tension pad upon the patient's skin to provide the substantially taut orientation thereto.

17. The method of claim 15, wherein in step (A), the tension isolating adjustable adapter is connected to the percutaneous device prior to inserting the percutaneous device through the patient's skin and fixating the percutaneous device within the patient's body.

18. The method of claim 15, wherein in step (A), the tension isolating adjustable adapter is connected to the percutaneous device after the percutaneous device is inserted through the patient's skin and fixated within the patient's body.

19. The method of claim 15, further comprising at least one of:
performing at least one external adjustment; or
applying at least one distraction force to the percutaneous device.

20. The method of claim 15, further comprising the steps of:
applying force to a segment of elastically deformable membrane to stretch the membrane to a stretched length that is greater than an original length of the membrane, wherein the elastically deformable membrane has a bonding material associated with at least a portion of a surface thereof;
applying the stretched membrane to the patient's, wherein the bonding material attaches the stretched membrane to the skin; and
releasing the stretch force on the membrane after application to the skin, thereby causing the skin having the membrane attached thereto to gather/compress.

21. The method of claim 15, wherein the percutaneous device is conductive, and wherein the method further comprises the step of:
forming an electrical circuit at an insertion site of the percutaneous device through the patient's skin and fixated within the body, the electrical circuit including a power source, the conductive percutaneous device, and tissue surrounding the conductive percutaneous implant;
monitoring at least one electrical parameter in the electrical circuit;
determining a presence of an infection due to the electrical parameter; and
varying electrical power within the electrical circuit responsive to determining the presence of the infection.

* * * * *